US009750528B2

(12) United States Patent
Scherkowski

(10) Patent No.: US 9,750,528 B2
(45) Date of Patent: Sep. 5, 2017

(54) HANDHELD DEVICE FOR REPEATED PUNCTURE OF HUMAN OR ANIMAL SKIN

(71) Applicant: MT.DERM GmbH, Berlin (DE)

(72) Inventor: Dirk Scherkowski, Berlin (DE)

(73) Assignee: MT. DERM GMBH (DE)

( * ) Notice: Subject to any disclaimer, the term of this patent is extended or adjusted under 35 U.S.C. 154(b) by 208 days.

(21) Appl. No.: 14/736,519

(22) Filed: Jun. 11, 2015

(65) Prior Publication Data

US 2015/0359559 A1    Dec. 17, 2015

(30) Foreign Application Priority Data

Jun. 12, 2014    (EP) .................................... 14172103

(51) Int. Cl.
| | |
|---|---|
| *A61B 17/34* | (2006.01) |
| *A61B 17/3209* | (2006.01) |
| *A61M 37/00* | (2006.01) |
| *A61B 17/00* | (2006.01) |
| *A01K 11/00* | (2006.01) |

(52) U.S. Cl.
CPC ... *A61B 17/32093* (2013.01); *A61M 37/0076* (2013.01); *A01K 11/005* (2013.01); *A61B 2017/00398* (2013.01); *A61B 2017/00477* (2013.01); *A61M 2210/04* (2013.01); *A61M 2250/00* (2013.01)

(58) Field of Classification Search
CPC . A01K 11/005; A61B 17/32093; A61B 17/34; A61B 2017/00398; A61B 2017/00477; A61M 2210/04; A61M 37/0076; A61M 37/0084
See application file for complete search history.

(56) References Cited

U.S. PATENT DOCUMENTS 4,204,438 A * 5/1980 Binaris ............. A61M 37/0076
30/362
4,796,624 A * 1/1989 Trott ................. A61M 37/0084
215/247

(Continued)

FOREIGN PATENT DOCUMENTS

CN    201426920 Y    3/2010
DE    29919199 U1    1/2000

(Continued)

*Primary Examiner* — Ryan J Severson
(74) *Attorney, Agent, or Firm* — Leason Ellis LLP

(57) ABSTRACT

A handheld device for repeated local puncture of human or animal skin, comprising a housing having a handle, a drive device in the housing supplied with a rotating movement about an axis of rotation by a driveshaft, a conversion mechanism coupled to the driveshaft to convert rotating movement into a driving movement along a driving movement direction, and a puncture device which is arranged in the housing and as a puncture needle, which is arranged on a needle shaft that can be moved back and forth repeatedly along a path of movement together with the puncture needle and is connected to the conversion mechanism, wherein the conversion mechanism has a rod crank device, and the stroke executed by the puncture element in moving back and forth is adjustable by altering a relative position between an axial direction of the axis of rotation and the direction of the driving movement.

16 Claims, 23 Drawing Sheets

(56) References Cited

U.S. PATENT DOCUMENTS

Figure 1:
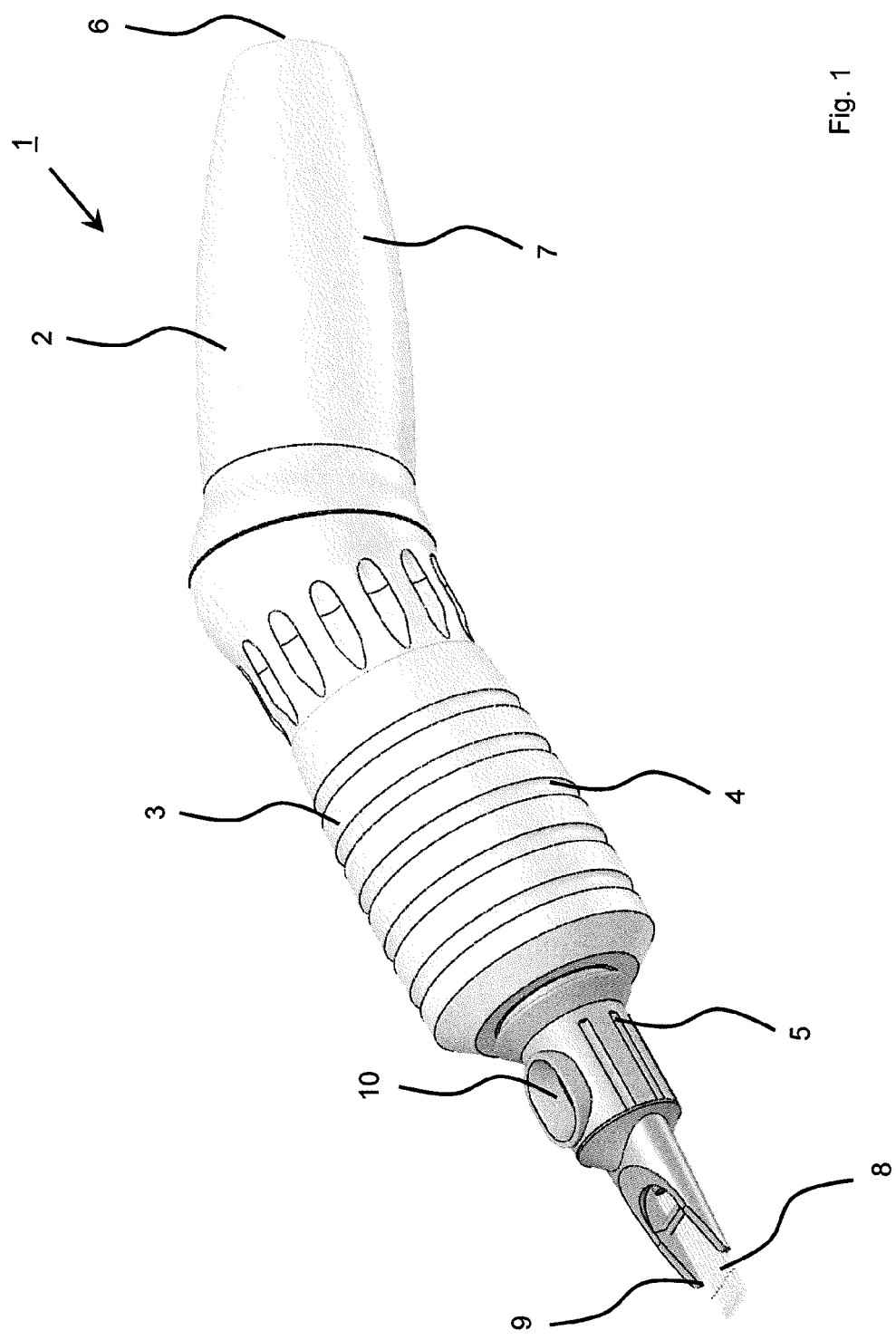
Figure 2A:
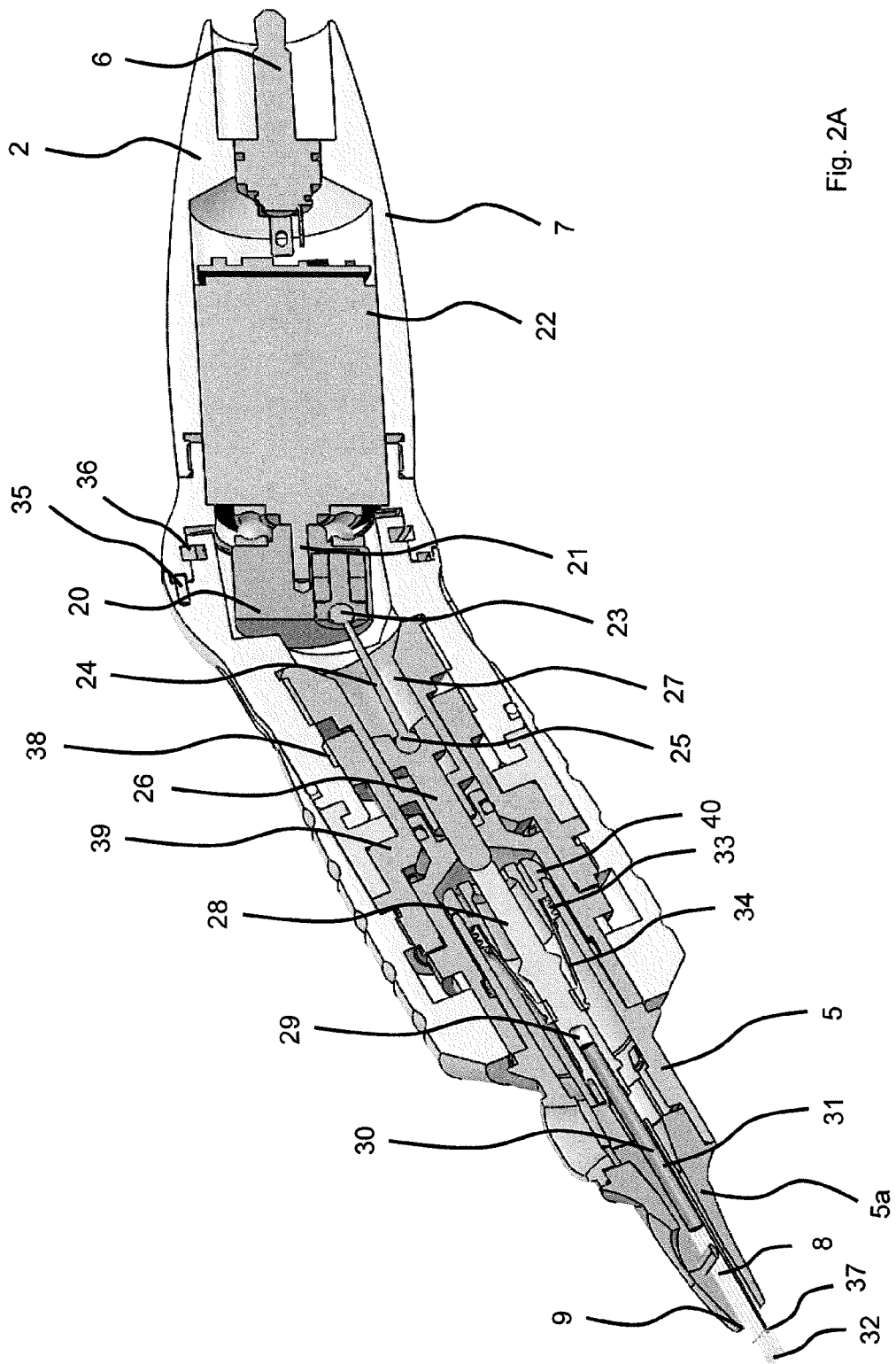
Figure 2B:
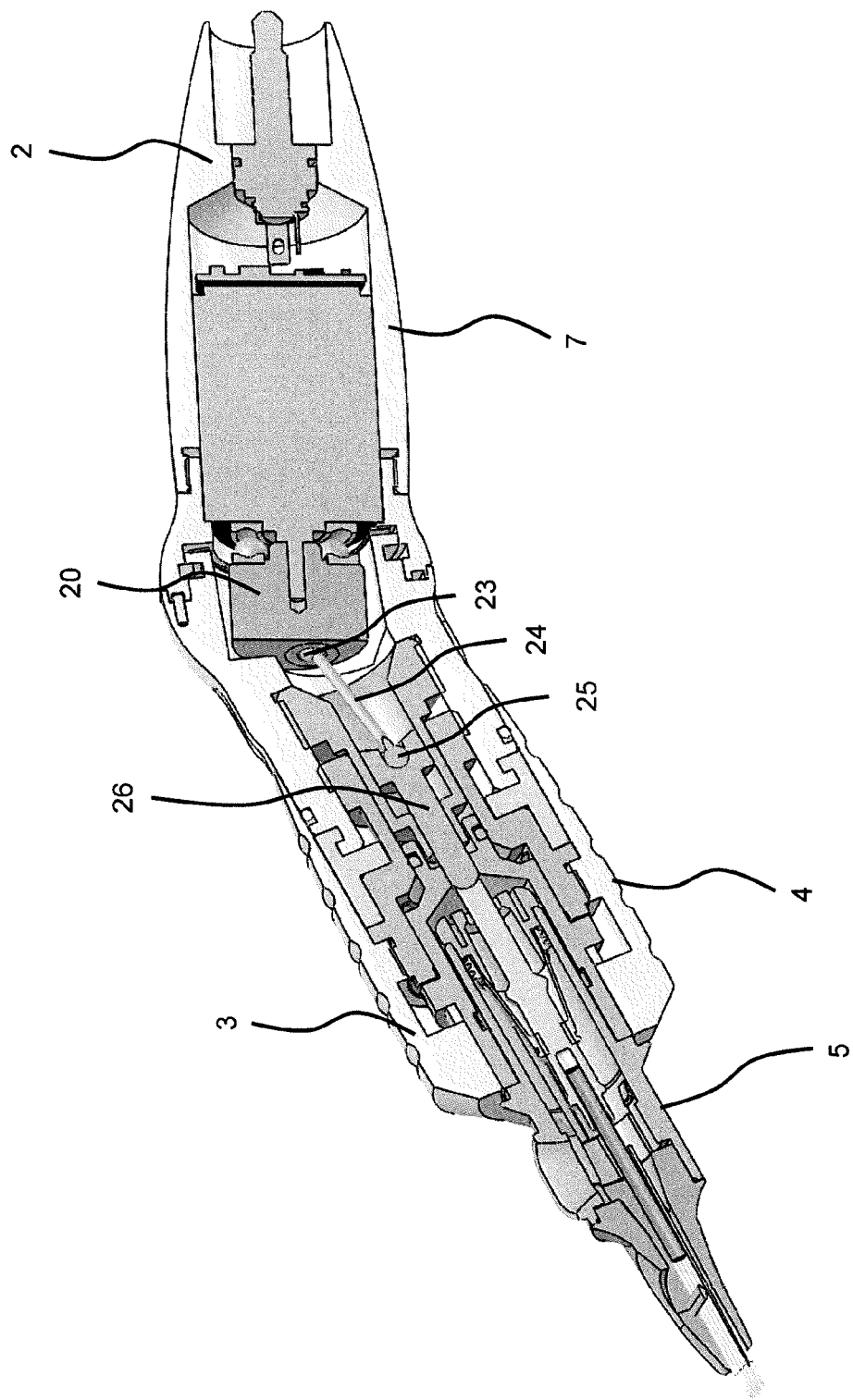
Figure 2C:
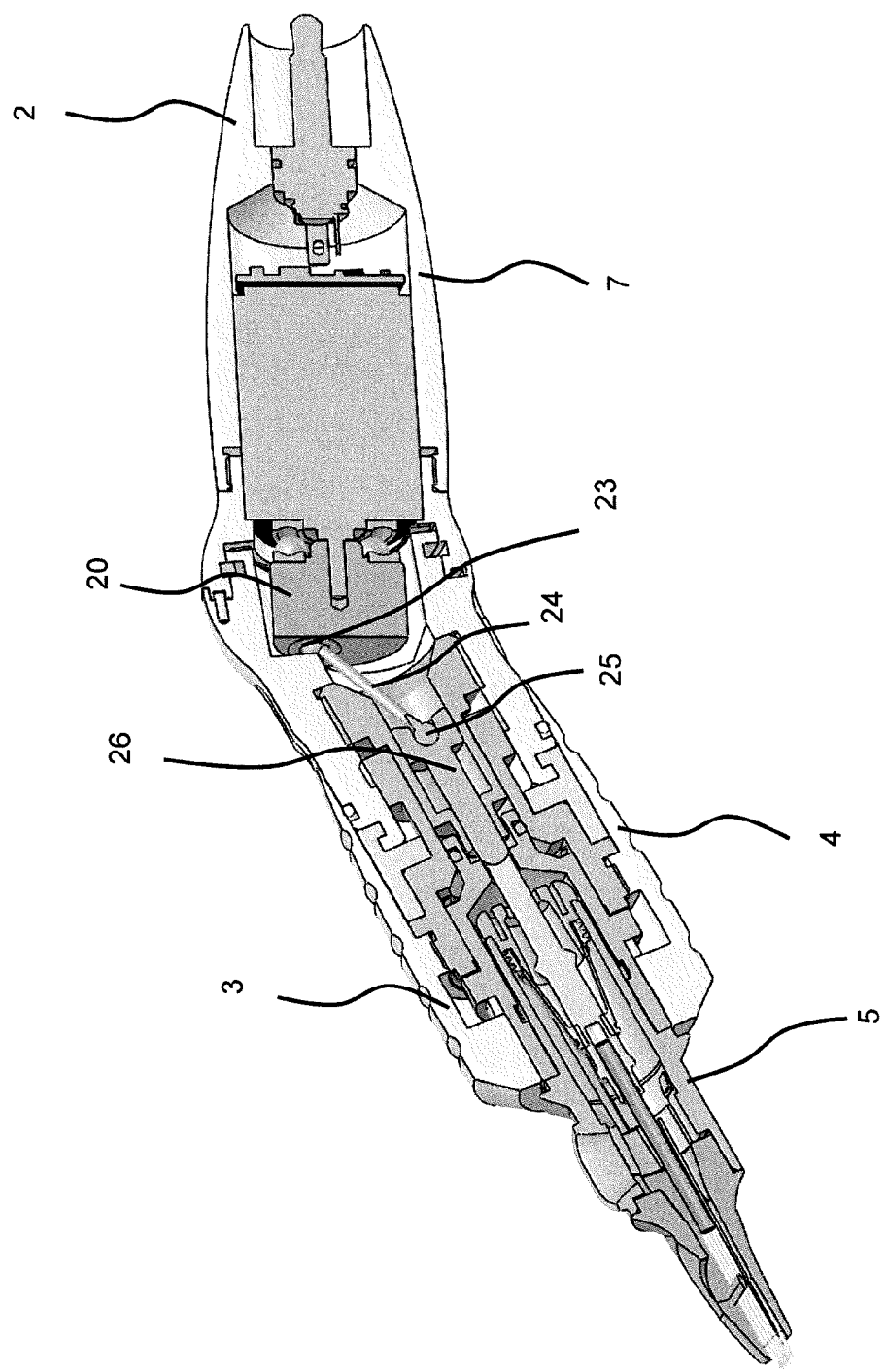
Figure 2D:
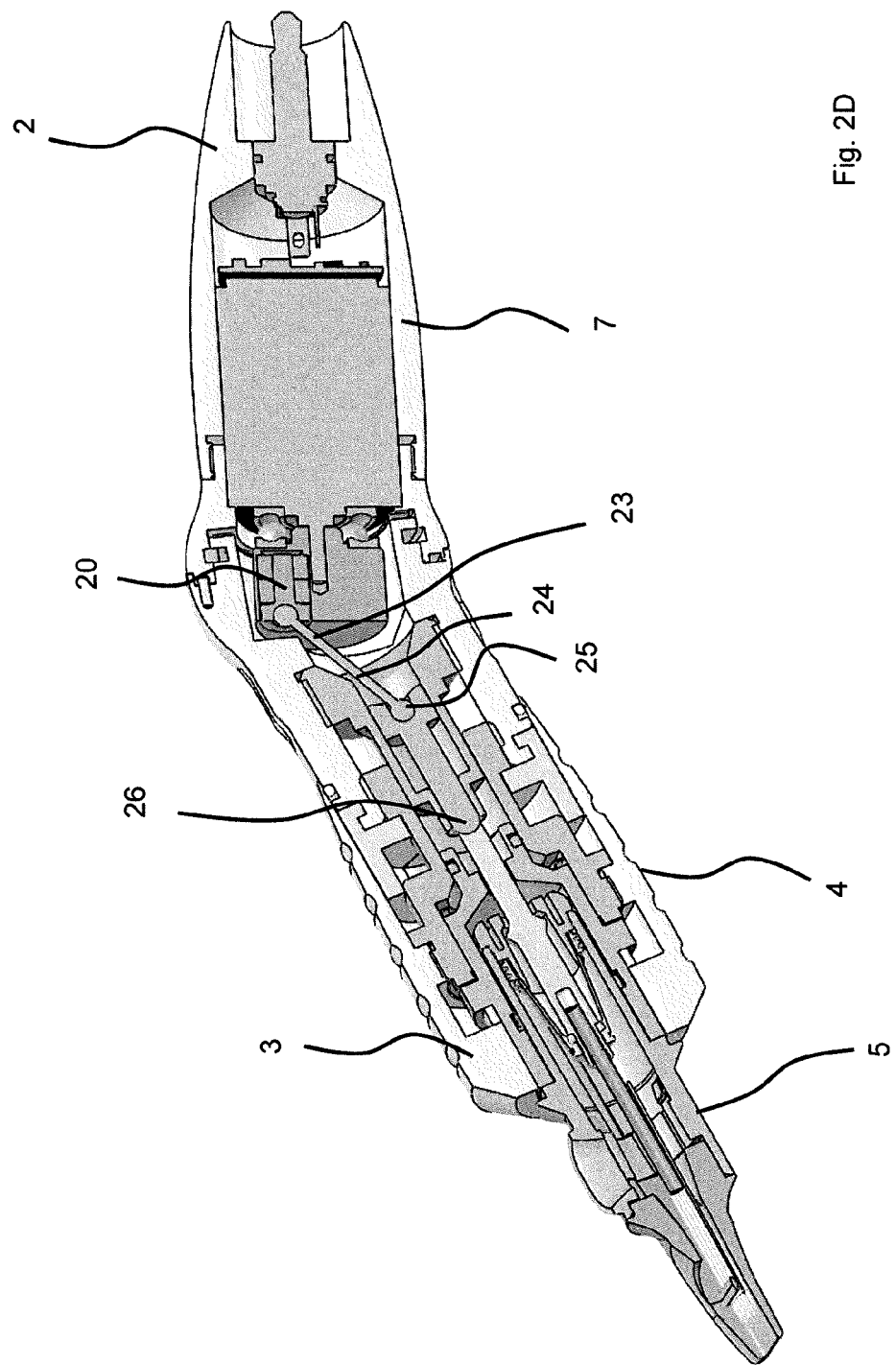
Figure 3A:
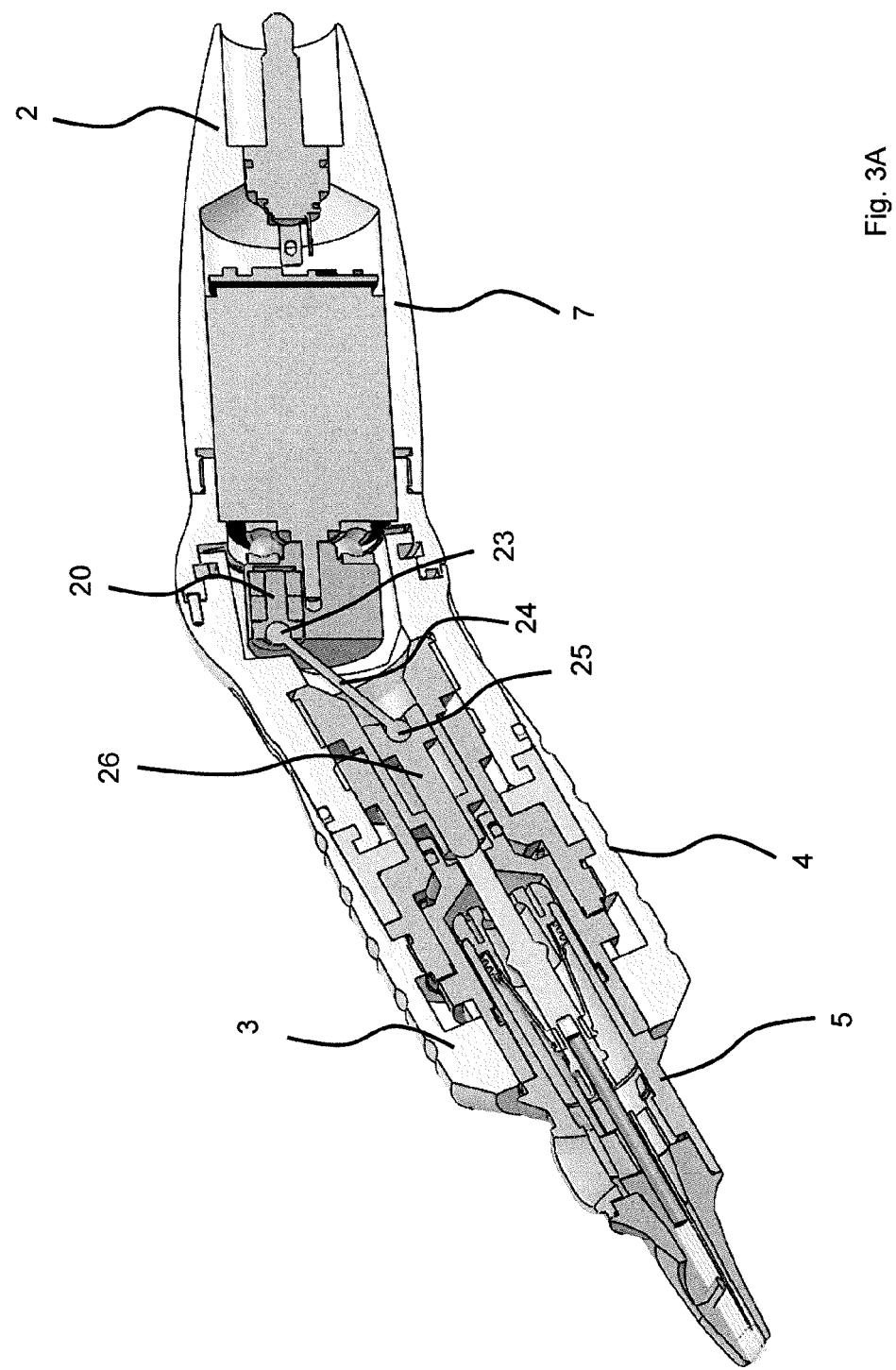
Figure 3B:
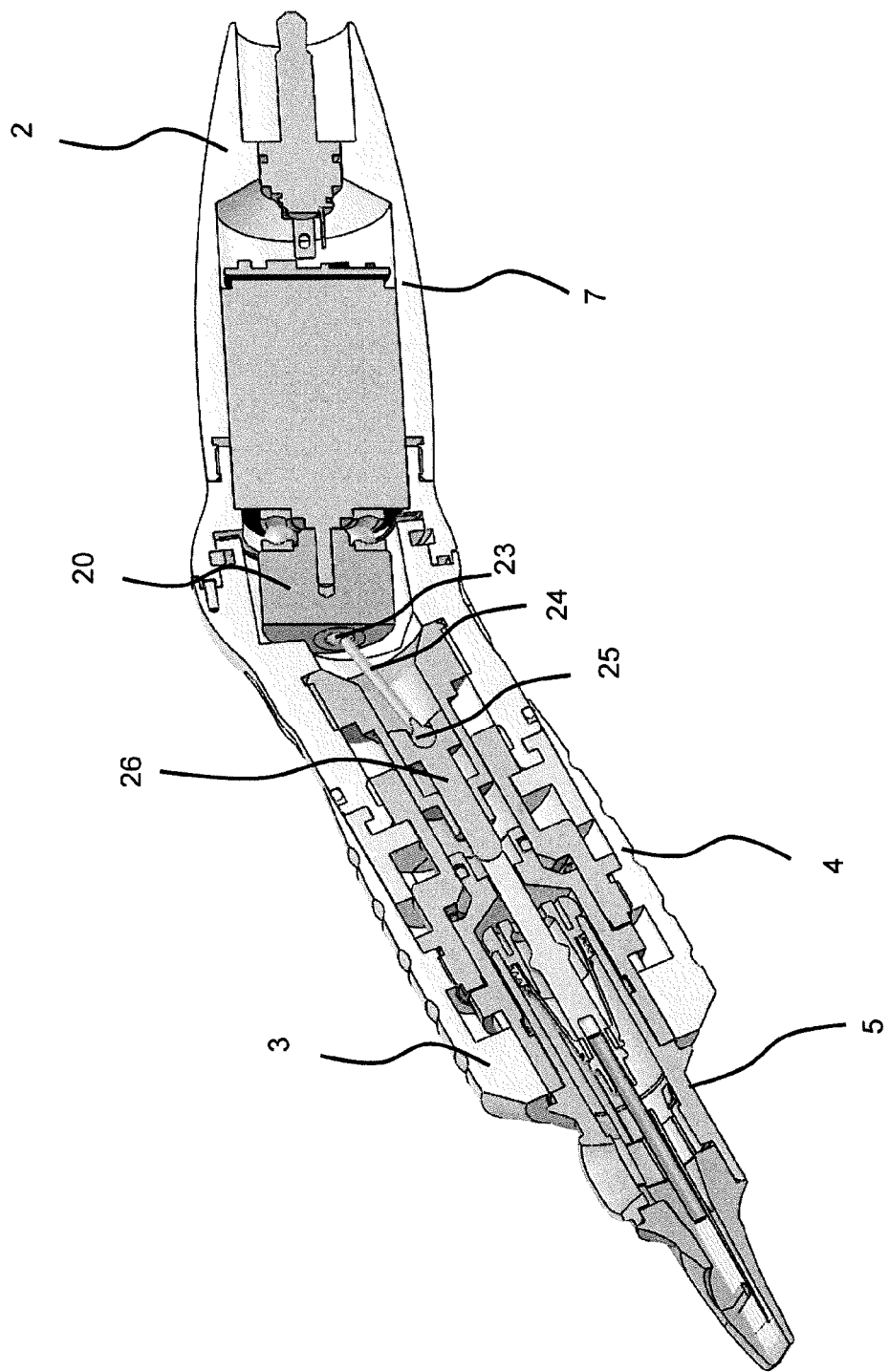
Figure 3C:
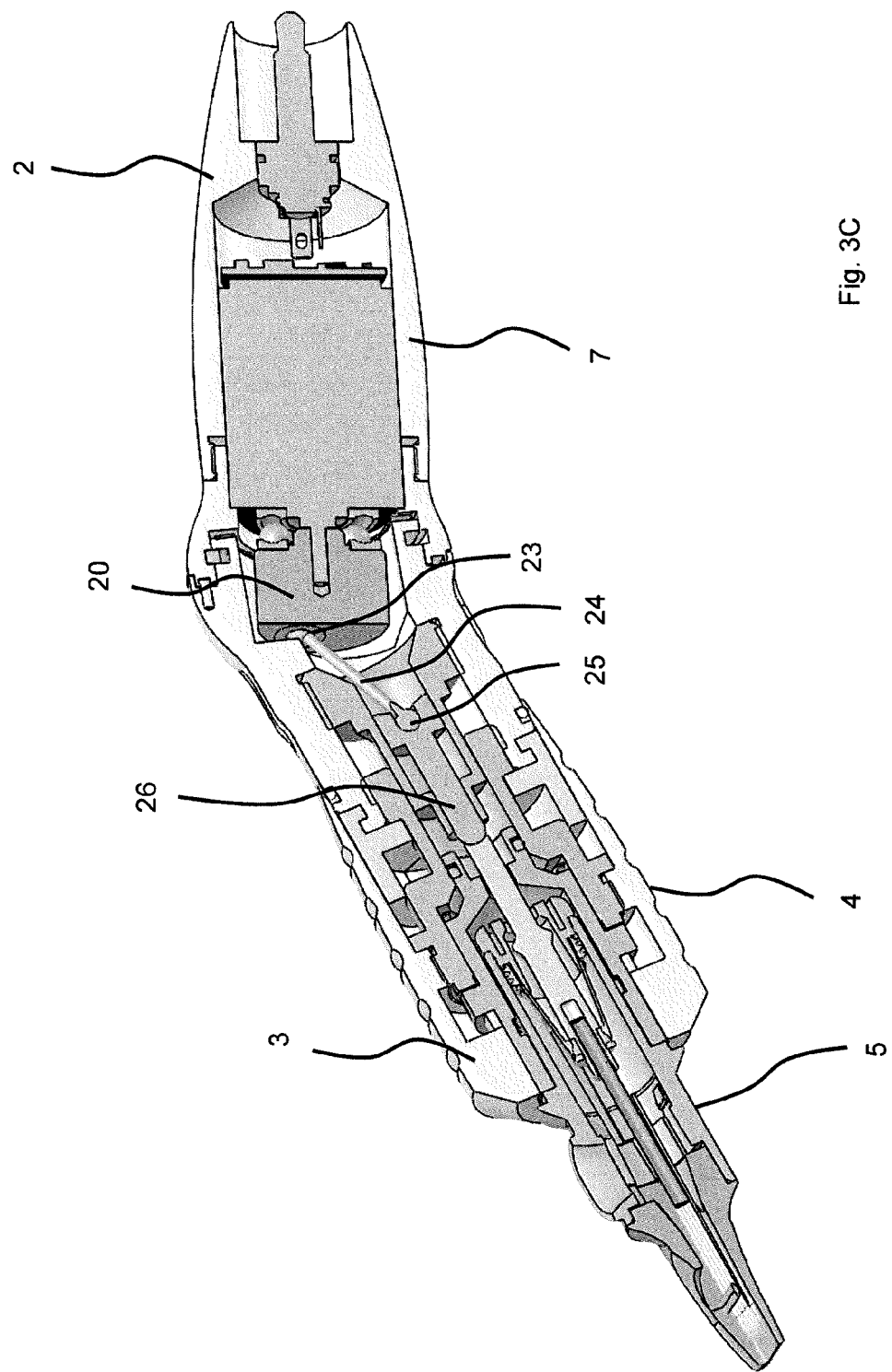
Figure 3D:
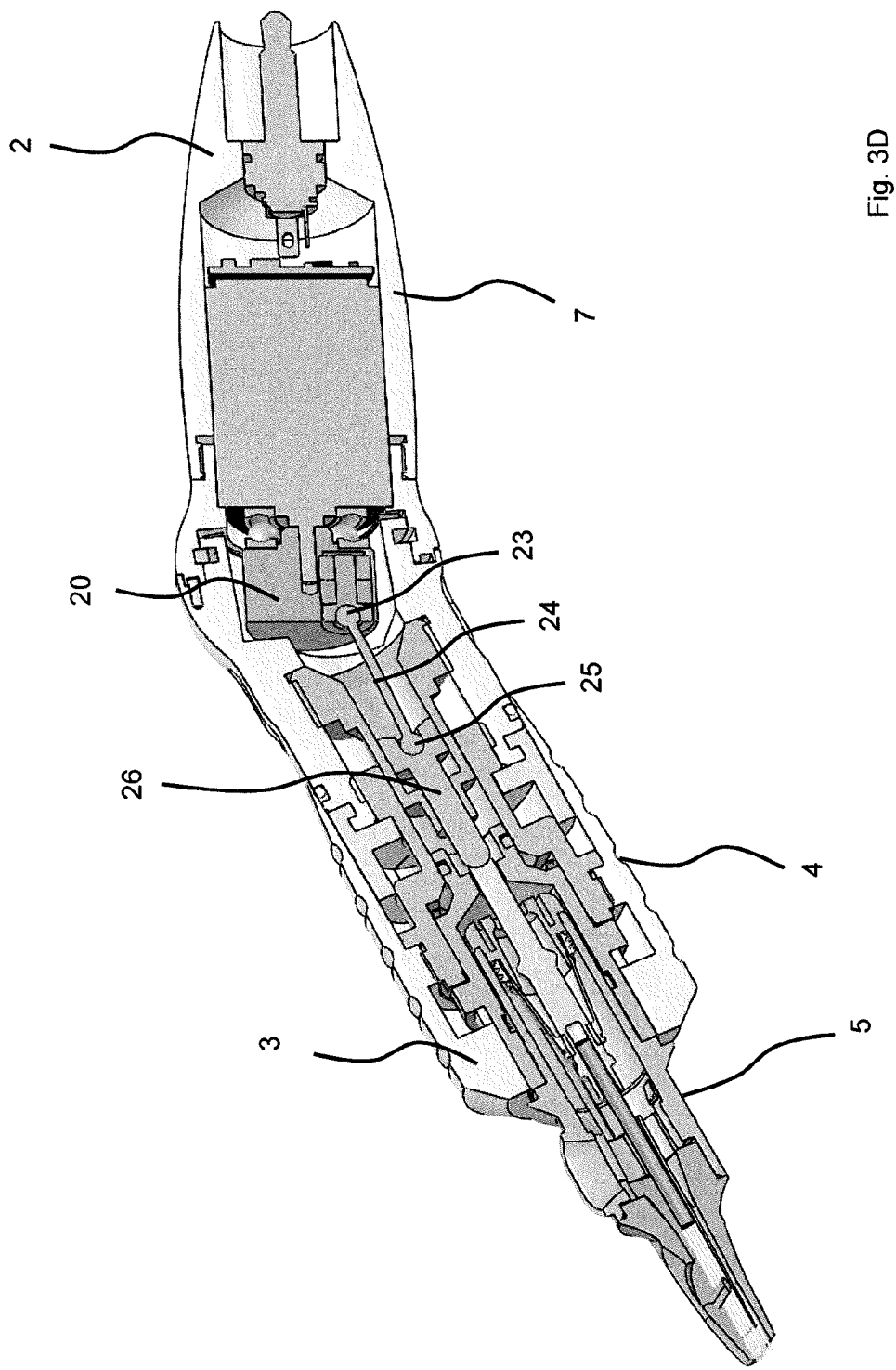
Figure 4A:
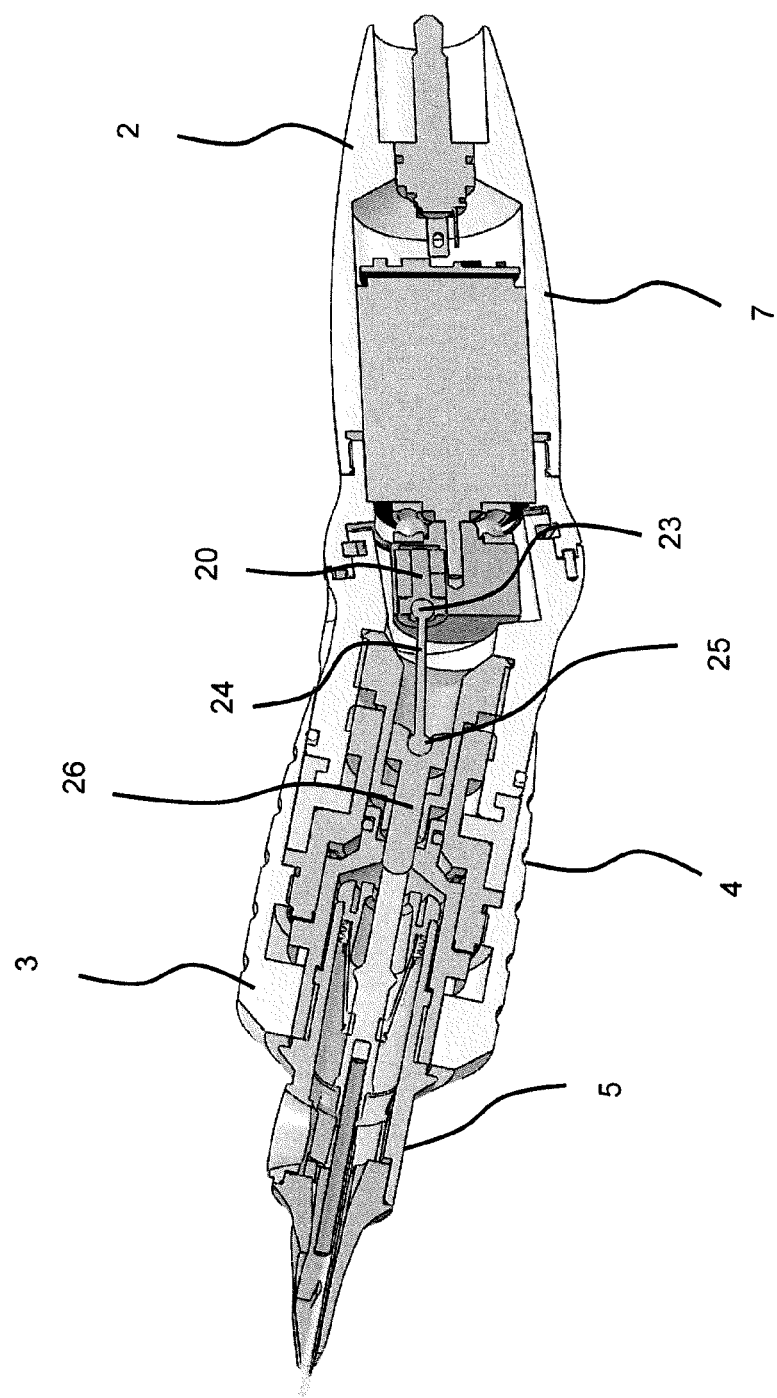
Figure 4B:
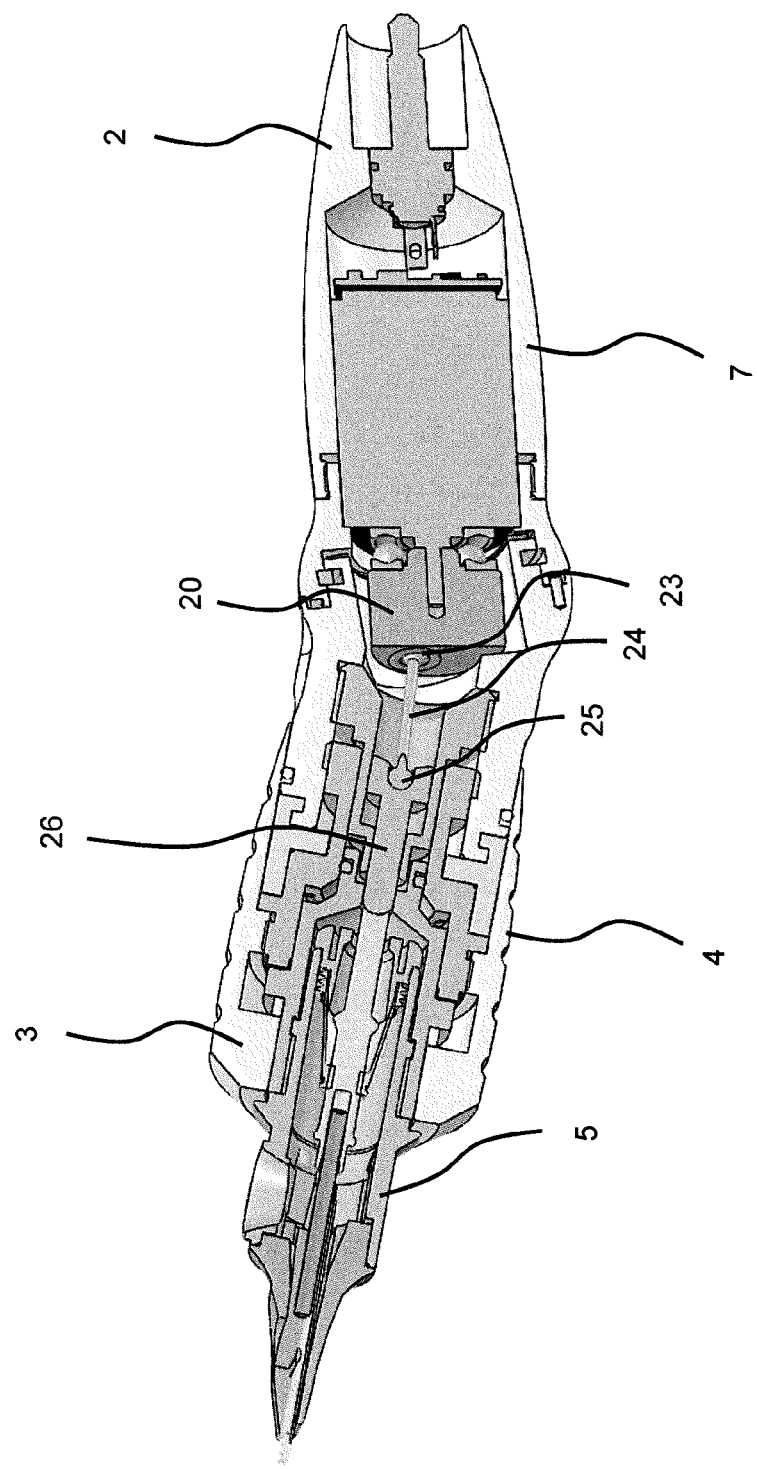
Figure 4C:
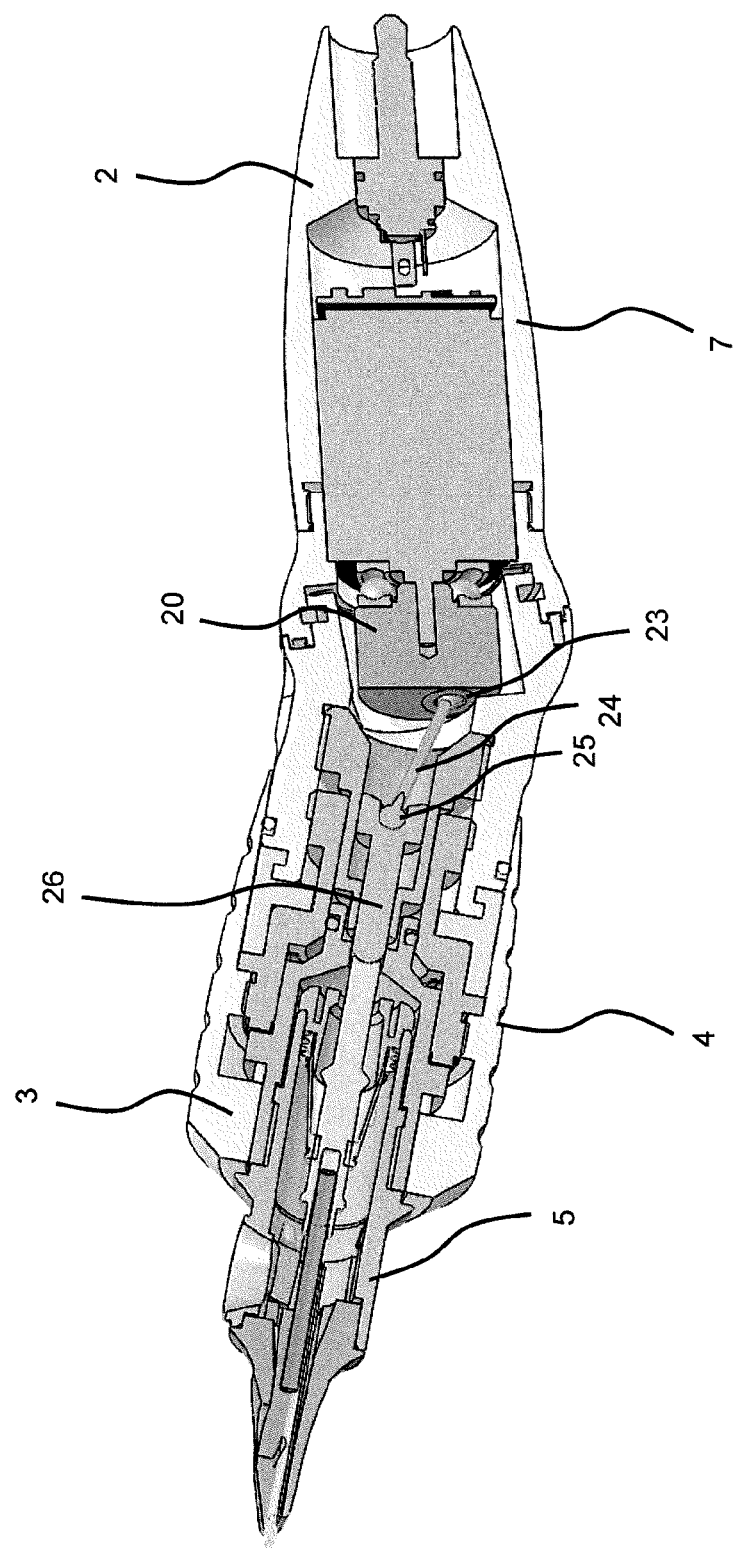
Figure 4D:
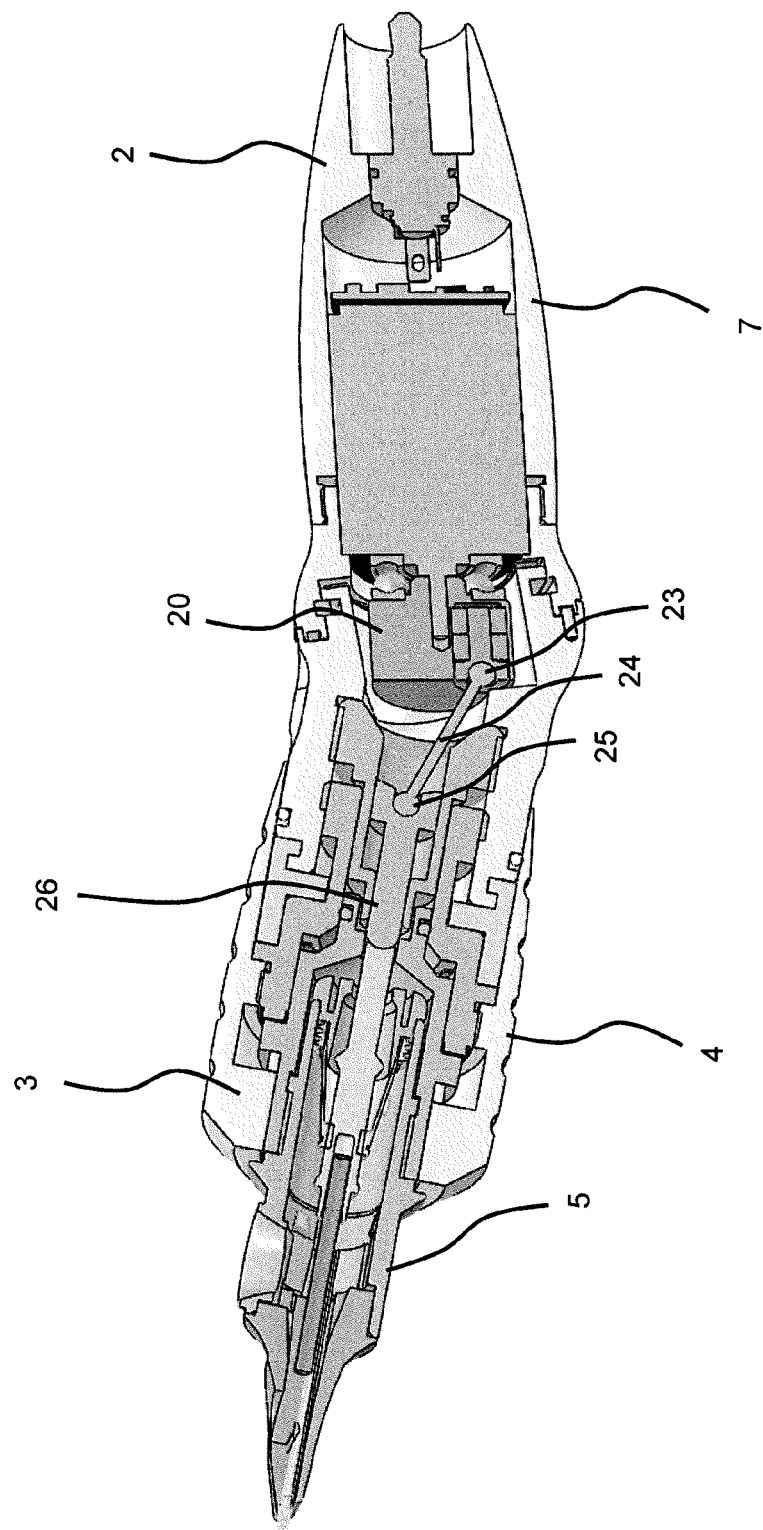
Figure 5A:
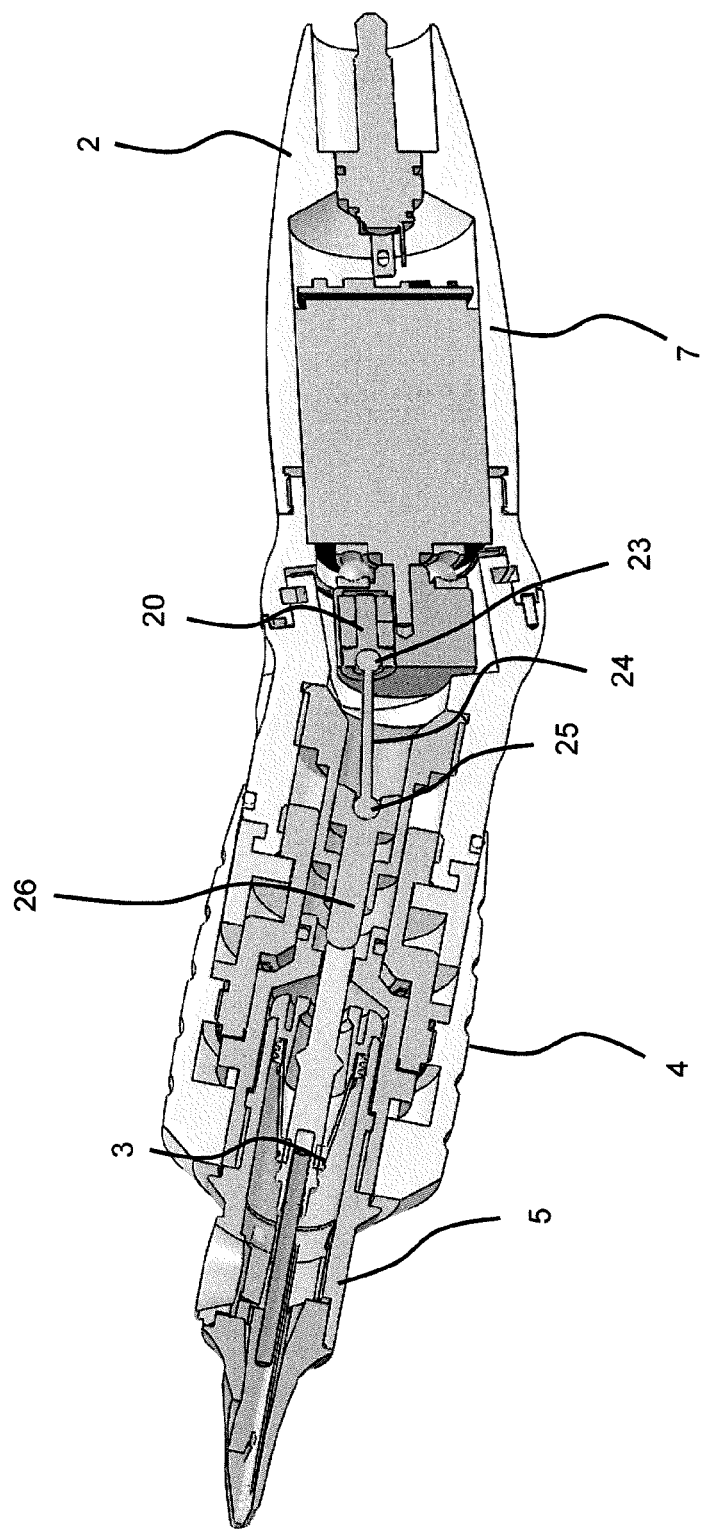
Figure 5B:
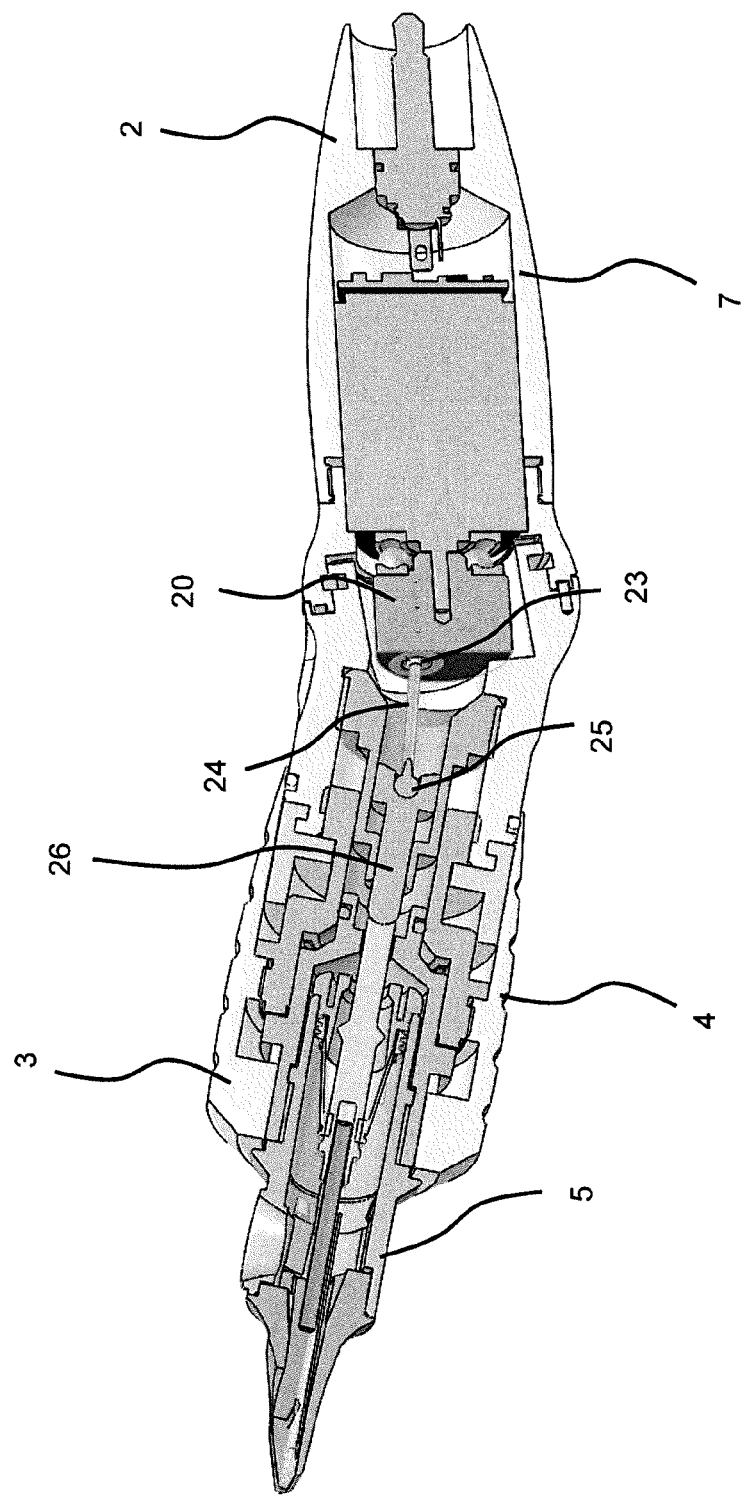
Figure 5C:
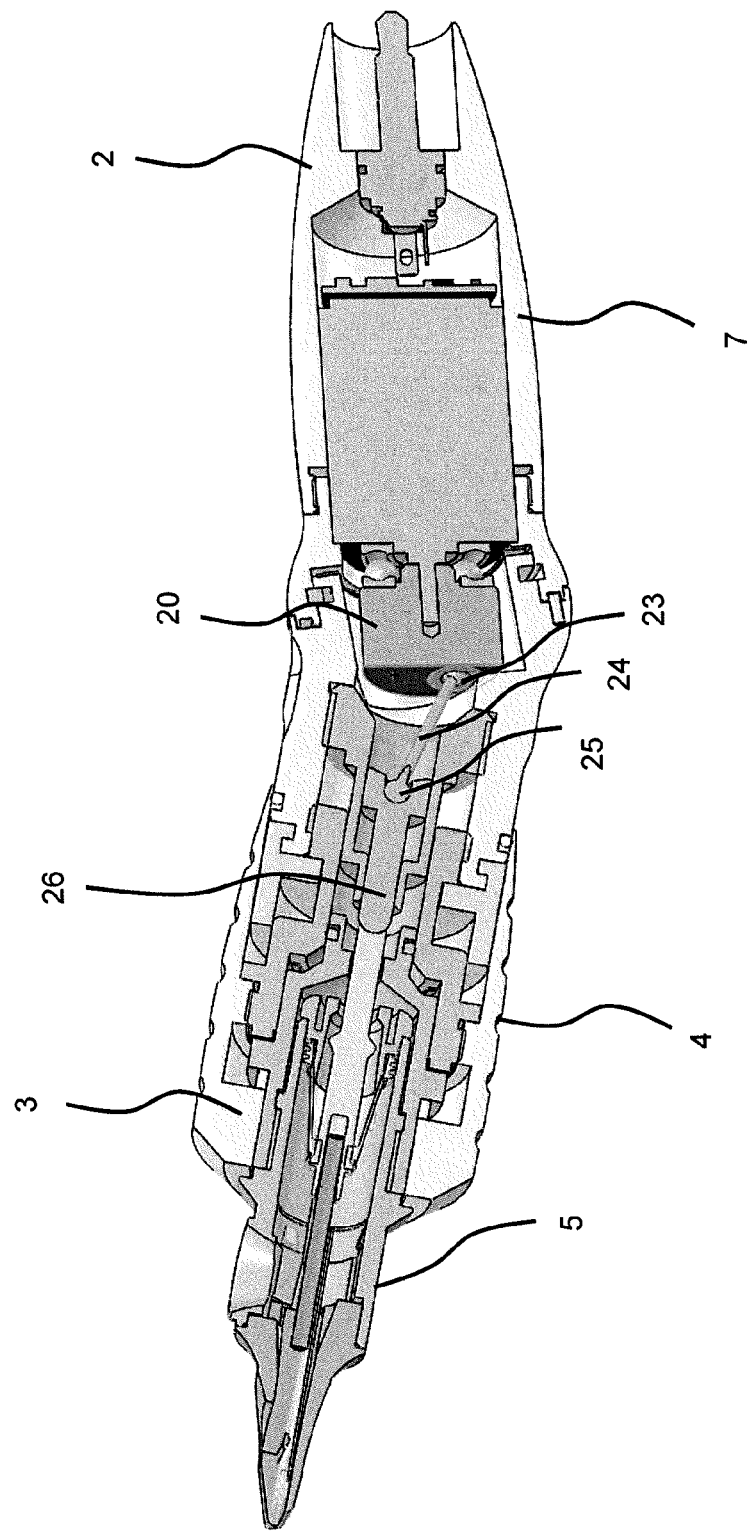
Figure 5D:
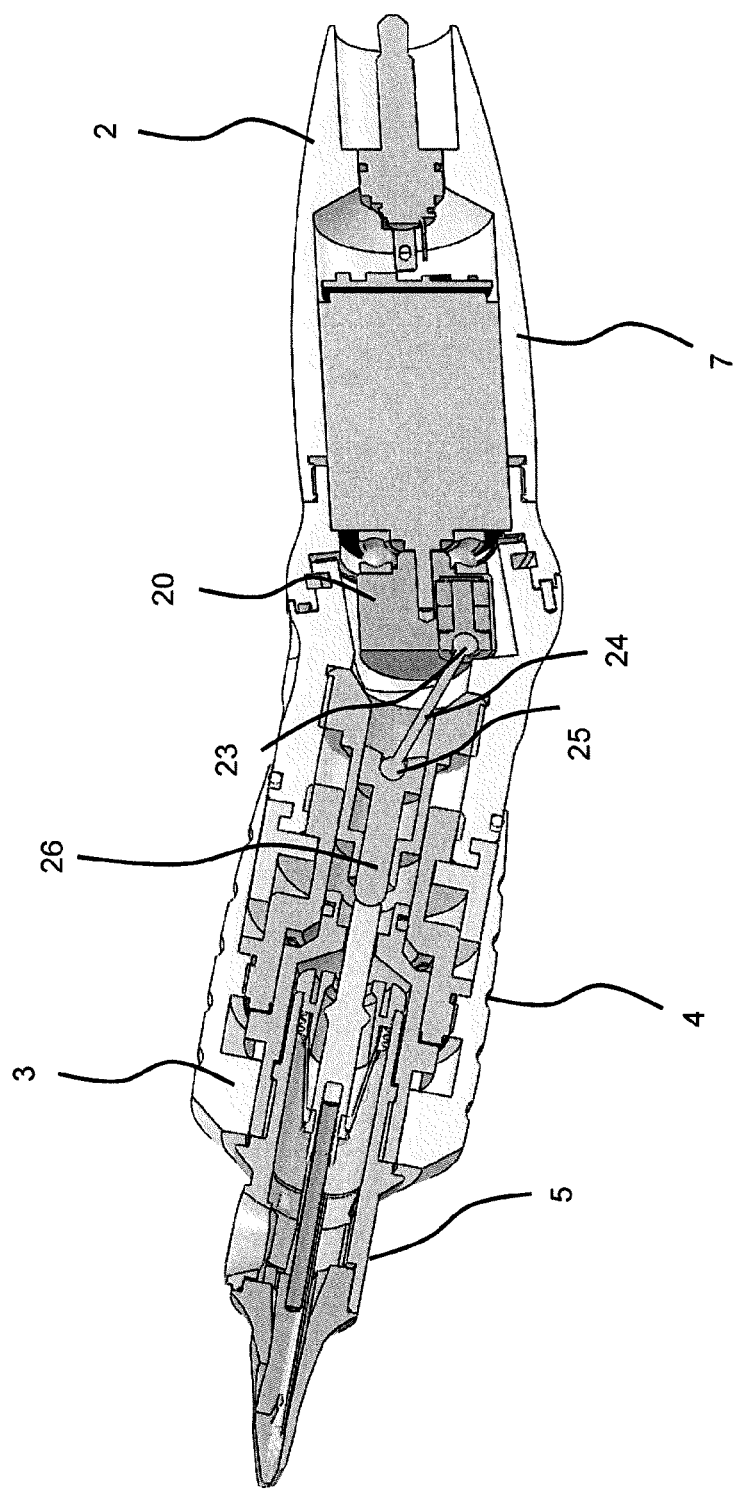

| | | | | |
|---|---|---|---|---|
| 4,914,988 | A * | 4/1990 | Chang | A01K 11/005 606/186 |
| 5,279,552 | A * | 1/1994 | Magnet | A61M 37/0076 604/47 |
| 5,472,449 | A * | 12/1995 | Chou | A61M 37/0076 606/186 |
| 5,776,158 | A * | 7/1998 | Chou | A61M 37/0076 606/186 |
| 6,033,421 | A * | 3/2000 | Theiss | A61M 37/0076 606/186 |
| 7,207,242 | B1 * | 4/2007 | Daigle | A61M 37/0076 30/362 |
| 7,695,486 | B2 * | 4/2010 | Dixon | A61M 37/0076 606/186 |
| 8,414,531 | B2 * | 4/2013 | Oginski | A61M 37/00 604/131 |
| 8,522,647 | B1 * | 9/2013 | Dixon | A61M 37/0076 30/362 |
| 9,114,239 | B2 * | 8/2015 | Lee | A61M 37/0076 |
| 9,393,395 | B2 * | 7/2016 | Miller | A61M 37/0076 |
| 9,504,814 | B2 * | 11/2016 | Frister | A61M 37/0076 |
| 2003/0195542 | A1 * | 10/2003 | Lee | A61M 37/0076 606/186 |
| 2004/0116953 | A1 * | 6/2004 | Dixon | A61M 37/0076 606/186 |
| 2007/0060937 | A1 * | 3/2007 | Liu | A61M 37/0076 606/185 |
| 2010/0191268 | A1 * | 7/2010 | Lee | A61M 37/0084 606/185 |
| 2011/0048174 | A1 * | 3/2011 | Lin | A61M 37/0084 81/9.22 |
| 2012/0123462 | A1 | 5/2012 | Lee | |
| 2015/0359559 | A1 * | 12/2015 | Scherkowski | A61B 17/32093 606/186 |
| 2015/0367118 | A1 * | 12/2015 | Scherkowski | A61M 37/0076 606/186 |
| 2016/0256674 | A1 * | 9/2016 | Scherkowski | A61M 37/0015 |

FOREIGN PATENT DOCUMENTS

| | | |
|---|---|---|
| DE | 20 2006 013148 U1 | 5/2007 |
| EP | 1495782 A1 | 1/2005 |
| GB | 2 044 879 A | 10/1980 |

* cited by examiner

HANDHELD DEVICE FOR REPEATED PUNCTURE OF HUMAN OR ANIMAL SKIN

This application claims the benefit of priority under 35 U.S.C. Section 119 of European Patent Application 14 172 103.5, filed Jun. 12, 2014, which is hereby incorporated by reference as if set forth in its entirety herein.

FIELD OF INVENTION

The present disclosure relates to a handheld device for repeated puncture of human or animal skin.

BACKGROUND

Devices for local puncture of human or animal skin are usually designed as handheld devices. Such handheld devices can be used for applying ink for tattooing and/or permanent makeup in the area of the skin surface. However, it is also possible to introduce cosmetic or medical active ingredients via the skin using such devices by puncturing the skin locally. In addition, such devices may be used without introducing any substance for stimulation of skin, for example.

A handheld device for local puncture of skin is known from the publication DE 299 19 199 U1, for example. The known handheld device has a handle piece, a drive device and a puncture needle, which is moved back and forth in relation to a needle nozzle tip with the help of the drive device during operation, wherein at least two modules detachably connected to one another are provided, and one of the two modules is designed as a reusable basic module with an integrated drive device. The other one of the two modules is a sterilized disposable module, into which all the components that could be infected by a customer's body fluids are integrated in the case of the known handheld device. In this way, the handheld device is made available in the form of two modules, one of which, namely the disposable module, can be replaced after being used, while the other module, which includes the drive device, is reused. With the help of the disposable module, the hygiene conditions in applying a tattoo and/or permanent makeup are improved, because all the parts that could potentially be contaminated by the customer's body fluids escaping during the treatment are replaced. This avoids having to replace the entire handheld device.

European Patent EP 1 495 782 A1 describes a drive module for a device for local puncture of human or animal skin, in which a drive device, which can generate a driving movement, and a converter mechanism coupled to the drive device are provided. The driving rotational movement is converted by the conversion mechanism into a back-and-forth movement that can be coupled to a puncture device that punctures the skin locally, thus permitting a repetitive movement of a puncture needle. The conversion mechanism comprises a function component, which executes a tumbling or tilting movement in the conversion of the movement, so that the driving force for moving the needle puncturing the skin locally in a back-and-forth direction is made available. In one embodiment, the function component is supported in a cantilevered fashion by means of a ball bearing. Unintended rotation of the function component, which may be caused by the driving rotational movement, is prevented with the known device by the fact that the function component mounted by means of the ball bearing or a protrusion formed on it engages in a recess. It has been found that this type of securing the function component during operation of the device leads to a substantial noise burden, which is caused in particular by the back-and-forth movement of the protrusion in the recess.

SUMMARY

It is an object to provide a handheld device for repeated local puncturing of a human or animal skin, in which the ease of operation of the handheld device is improved, in particular with regard to interfering concomitant phenomena, such as noise or vibration of the handheld device, for example.

According to an aspect, a handheld device for repeated local puncture of human or animal skin is provided, comprising a housing with a handle being formed on it. During operation of the handheld device, the user grips the handle to guide the handheld device. The handheld device may also be referred to as a tattooing device in the event of its use to form tattoos or permanent makeup. Other applications involve local puncture of the skin to introduce a cosmetic or medical active ingredient. Active ingredients can be injected through cannulas. However, the handheld device may also be used for local puncture of human or animal skin without introducing any substance, for example, for stimulation of skin. The housing holds a drive device, with which a rotating driving force is supplied by means of a driveshaft. An electric motor may be provided for this purpose.

A conversion mechanism, which is arranged in the housing and is equipped to convert the rotating movement (rotating drive force) about an axis of rotation into a driving movement along a direction of driving movement, is connected to the driveshaft. The driving force thereby made available is an axially directed driving movement in one exemplary embodiment.

In addition, a puncture device, which is accommodated in the housing and has a puncture element provided with one or more puncture needles arranged in a needle receptacle, is provided. In the case of a plurality of puncture needles, they may be arranged in groups, in which the needles are close to one another. However, the distribution of needles or needle groups over the surface of a needle plate may also be provided. In this case, the needle receptacle is formed by a needle plate. The needle receptacle is connected to the conversion mechanism and is moved repeatedly back and forth along a path of movement, for example, a linear path of movement, for example, in an axial direction, together with the one or more puncture needles during operation.

The conversion mechanism has a rod crank device, which is coupled to the driveshaft. A rod crank operation can be implemented in this way. A stroke movement executed by the puncture element in the back-and-forth movement is adjustable by varying a relative position between an axial direction of the axis of rotation and the direction of the driving movement.

The stroke can be adjusted manually or by means of an adjusting drive.

With the handheld device the drive device, in particular an electric motor may be accommodated or received in a housing section positioned across the handle on the housing. The drive device may be equipped to provide a rotating driving movement of at least approximately 1800 min$^{-1}$ (30 Hz) during operation.

In an exemplary embodiment of the rod crank device, a coupling element may be provided on the drive side, such that this coupling element is coupled to the driveshaft and rotates accordingly during operation of the rotating driving movement of the driveshaft. In one embodiment, the coupling element on the drive side may be embodied as a drive disk. A proximal end of a connecting rod of a rod connector of the rod crank device can be coupled in an articulated joint to the drive-side coupling element, such that the proximal end of the connecting rod is moved around the axis of rotation of the driveshaft in the rotation of the drive-side coupling element on a closed path of movement, in particular a circular path. The drive-side coupling element can sit directly on the driveshaft, so that it also moves when the latter is rotated. Then the proximal end of the connecting rod runs on its closed path of movement around the direction of the axis of rotation of the driveshaft. A distal end of the rod connector can be coupled in an articulated joint to an output-side coupling element, which is then coupled to the needle shaft for transmission of the axially directed driving movement, so that the needle shaft is moved back and forth during operation according to the axially directed driving movement.

The articulated connection between the proximal end of the connecting rod and the drive-side coupling element and/or the articulated connection between the distal end of the connecting rod and the output-side coupling element can be set up to allow a spatial pivotability of the respective connecting rod end with respect to the coupling element.

The housing may be made of a single material or a combination of different materials, which include metal and plastic in particular. Housing sections can be releasably mounted, in order to release regions of the housing interior, for example, for replacement or repair purposes. A cable connection may lead out of the housing, to be used for connecting the handheld device to an external control unit. The cable connection may serve to connect an electric motor to a power source, in particular via the control unit. The cable connection may have a data cable by means of which electronic data can be exchanged between the handheld device and the control unit. Alternatively or additionally such a data exchange between the handheld device and the control unit may also be carried out over a wireless data link using Bluetooth technology, for example. Control units for handheld devices for repeated local puncture of human or animal skin are known as such in various embodiments and therefore will not be discussed further here.

In the various embodiments, the coupling between the conversion mechanism and the needle receptacle, which may be formed with a needle shaft, may be designed, so that, because of the driving force that is supplied, the needle receptacle is not only moved forward during operation but is also retracted by means of the conversion mechanism, comprising the coupling component. In this embodiment, the conversion mechanism itself provides a restoring force. Alternatively or additionally, it is possible to provide that the restoring force is supplied at least partially by an elastic element, for example, a spring or a diaphragm. In this embodiment, the forward movement of the needle receptacle with one or more puncture needles takes place against an elastic prestress, which then in turn contributes toward the reverse movement or is solely responsible for it. The elastic element automatically contracts in the extraction of the puncture element after being stretched and thus causes the reverse movement of the one or more needles.

The conversion mechanism may have rotational decoupling. The rotational decoupling ensures that, starting from the rotating movement of the drive-side coupling element, no torque is transmitted to the needle shaft with the one or more needles received therein. The uncoupling from the rotating driving movement may be provided in a mechanical chain of the conversation mechanism at one or more transitions between neighboring elements of the transmission chain.

The articulated coupling between the proximal end of the connecting rod and the drive-side coupling element may be designed to be rotationally decoupled. Rotational decoupling can be designed with the help of a ball head joint in which a ball head is held in a ball socket, so that it can rotate. In conjunction with the proximal end of the connecting rod, the function is rotation about the longitudinal axis of the connecting rod in particular. The ball head may be provided on the proximal end of the connecting rod or on the drive-side coupling element. Instead of accommodating a ball head in the ball socket, the ball head may be provided with a ball shell, which sits on it and which is in turn held in the ball socket so that it can rotate, whereas the ball shell is fixedly secured on the ball head.

The articulated coupling may be configured to be rotationally decoupled between the distal end of the connecting rod and the output-side coupling element.

A refinement preferably provides for the proximal end of the connecting rod and the distal end of the connecting rod to be accommodated in a rotationally decoupled manner on the rod connector. In this embodiment one of the ends of the connecting rod can rotate about the longitudinal axis of the rod connector, independently of the other end of the connecting rod.

In one embodiment, the proximal and distal ends of the connecting rod are thus received rotatably in a connecting rod sleeve with a section extending toward the center of the rod connector.

The proximal end of the connecting rod may be connected in an articulated manner to the drive-side coupling element by means of a ball joint and/or the distal end of the connecting rod is connected in an articulated manner to the output-side coupling element by means of a ball joint.

It may be provided that the output-side coupling element is connected by a rigid connection to the needle shaft or is designed in one piece with it. The output-side coupling element may be arranged with the needle shaft in a joint guide in the housing. Alternatively separate guides for the output-side coupling element and for the needle shaft may be provided in the housing. The one or more guides may be formed in parallel or obliquely to the axis of rotation of the driveshaft. In the case of a one-piece design, the articulated coupling of the distal end of the connecting rod may be arranged on an end face of the needle shaft facing the drive device. The connection between the output-side coupling element and the needle shaft may be designed to be releasable or non-releasable. A mechanical and/or magnetic coupling may be used for the connection.

A retriever device may be coupled to the needle shaft. The retrieval device may have a spring element, for example. With the help of the retrieval device a restoring force for the needle shaft and/or the output-side coupling element may be made available.

The drive axle (drive side) may be arranged so that it is not parallel with the direction of movement (output side), for example, an axially directed movement. An inclined position of the two axes to one another is formed in this way. The angle between the direction of the drive axle (axial direction of the driveshaft) and the direction of the movement, which is different from zero degrees, may be adjustable. By adjusting the angle (change in the inclined position) the stroke or lift setting can be executed. To adjust the angle, it is possible to provide in one exemplary embodiment that housing parts connected to one another in an articulated connection are supported relative to one another, whether manually or by means of a drive. In one embodiment the angle between the direction of the drive axle and the direction of movement is different from 90 degrees.

A linear path of movement in advancing and retracting the needle shaft and the drive axle may be arranged so they are offset in parallel to one another. For example, a stroke setting can be implemented here by means of a change in the parallel offset, i.e., a relative displacement for the change in distance of the directions/axes running in parallel. To do so, for example, an output-side coupling element accommodating the output side end of the connecting element may be accommodated in an eccentric position in a component that is mounted to at least rotate, so that by rotating the eccentric position can be varied, which changes the parallel offset.

The maximum needle or puncture element projection beyond the tip of the puncture needle may be adjustable with respect to a front housing opening.

The housing may be formed with a plurality of housing modules, wherein the drive device is arranged in a drive module, and the puncture device is arranged in a puncture module. The housing modules may be releasably connected to one another. In one embodiment of housing modules connected detachably to one another, the puncture module, which can also be referred to as the needle module may be designed as a sterilized disposable module. A housing part or module with a handle may also be formed as a releasable module. In addition to the puncture module or needle module, which may be arranged detachably on the housing part, the housing part may be designed as an additional disposable module or as a reusable module. It is also conceivable for the puncture module and the housing part to be designed with a handle as one unit, for example, even in one piece.

DESCRIPTION OF EXEMPLARY EMBODIMENTS

Figure 6:
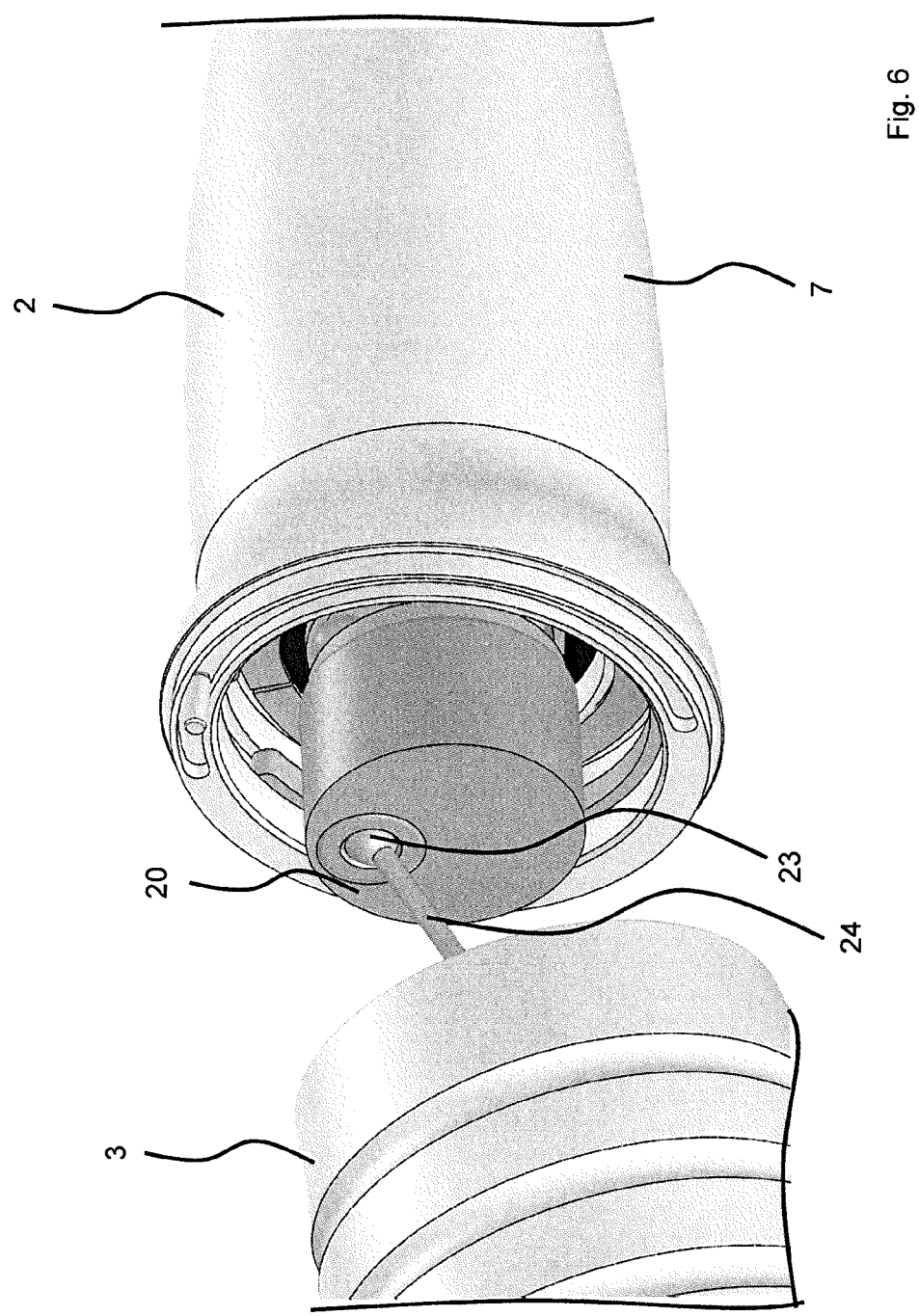
Figure 7:
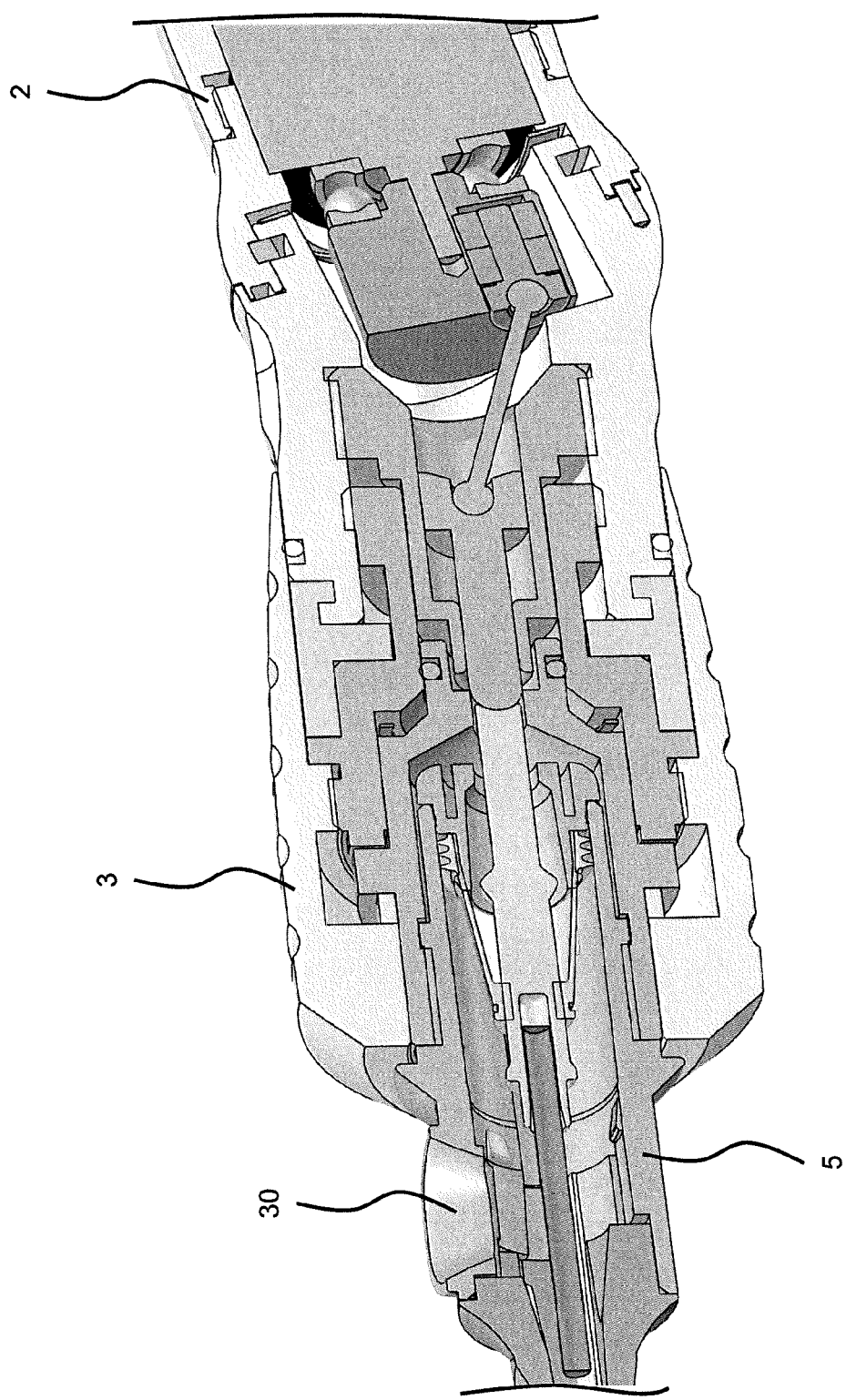

Additional exemplary embodiments are explained in greater detail below with reference to figures of a drawing, which:

FIG. 1 shows a schematic diagram of a handheld device for repeated local puncture of human or animal skin from the side, FIGS. 2A to 2D show a schematic diagram of the handheld device in a sectional view in a variety of operating positions, where a working stroke and a needle protrusion are set at the maximum setting, FIGS. 3A to 3D show schematic diagrams of a handheld device in various working positions in a sectional view, wherein the working stroke is set at its maximum and the needle protrusion is set at its minimum, FIGS. 4A to 4D show schematic diagrams of a working device in various working positions in sectional views, wherein the working stroke is set at the minimum and the needle protrusion is set at the maximum, FIGS. 5A to 5D show schematic diagrams of a working device in various working positions in sectional views, wherein the working stroke and the needle protrusion are set at the minimum, FIG. 6 shows an enlarged perspective diagram of a coupling region, FIG. 7 shows an enlarged sectional diagram of one part of a handheld device, FIGS. 8A to 8D show schematic diagrams of an arrangement of components for a handheld device in various working positions, such that, when advancing and retracting the needle shaft, the drive axle is arranged in parallel to and offset from a linear path of movement.

FIG. 1 shows a schematic diagram of a handheld device 1 for repeated local puncture of human or animal skin. A handle or handpiece 4 is formed on the outside of a housing 2 on a front housing part 3. The front housing part 3 detachably holds a puncture module or needle module 5, which can be designed as a disposable module and is secured on the front housing part 3 by means of a bayonet closure, for example.

In the embodiment shown here, an electric motor is accommodated in the housing 2 as a drive that can be connected to a power supply by means of a plug device 6. It is possible to provide that signal connections or control connections are implemented by the plug device 6, for example, for connecting the handheld device to an external control unit (not shown) by means of which an rpm control can be provided for the electric motor, for example.

The housing 2 has a rear housing part 7 which may be designed as a drive module with the electric motor. The front and the rear housing parts 3, 7 can be detachably connected to one another.

One or more needles 8 providing for a puncture element are received in the puncture module or needle module 5 in the usual way so that they can be extracted and retracted through a front housing opening 9 during operation. The one or more needles 8 are in turn arranged in the front housing part 3 on a needle receptacle (not shown) in the usual way.

An insertion opening 10, by means of which an ink can be introduced in one possible mode of operation, is provided on the puncture module or needle module 5.

FIGS. 2A to 2D show the handheld device 1 in various working positions in sectional views. The various working positions differ in different rotational positions of a drive-side coupling element 20 which sits on a drive shaft 21 of a drive device 22. The drive device 22 is an electric motor, for example. With the help of the drive device 22 the drive shaft 21 is induced to a rotational movement which causes the drive-side coupling element 20 to rotate. The drive-side coupling element 20 is connected in an articulated joint to a proximal connecting rod end 23 of a rod connector 24. In the embodiment shown here, the articulated connection is established with the help of a ball joint. Because of the rotating movement of the drive-side coupling element 20, the drive-side end 23 of the connecting rod moves around the driveshaft 21 on a closed path of movement. FIGS. 2A to 2D show different rotational positions of the drive-side coupling element 20.

A distal end 25 of the rod connector 24 is mounted on an output-side coupling element 26 with an articulated joint, also with the help of a ball joint, in the exemplary embodiment shown here. A conversion mechanism with which the rotating driving movement of the driveshaft 21 is converted into an axial back-and-forth movement of the output-side coupling element 26 in a guide 27 is provided with the help of the drive-side coupling element 20, the output-side coupling element 26 and the rod connector 24. Because of the rotating movement of the drive-side coupling element 20, a repetitive back-and-forth movement of the output-side coupling element 26 is induced, based on the rotating movement of the drive-side coupling element 20, by means of the coupling with the rod connector 24. The axial movement of the output-side coupling element 26 thereby executed has a direction of movement which is not parallel to the axial direction of the driveshaft 21 but instead is at an angle thereto (inclined position).

An intermediate piece 28 on whose front side a needle shaft 30 of a puncture device 31 is accommodated in a receptacle 29 is coupled to the output-side coupling element 26. The puncture device 31 has a plurality of needles 8, which are in turn accommodated on the needle shaft 30. In another embodiment, just one needle may be provided. During operation, a puncture needle tip 32 moves back and forth in a front housing opening 9 of the needle module 5 on which a module tip 5a is formed.

A reset device 33 is provided with a diaphragm 34. The diaphragm 34 is stretched in the axial direction when the needle shaft 30 with the needles 8 accommodated therein is moved forward, such that the diaphragm 34 supplies a restoring force that exceeds the prestressing force. This restoring force acts in addition to a reverse movement induced by the rod connector 24.

In the embodiment depicted in FIGS. 2A to 2D, a working stroke or lift of the needle shaft 30 is set at the maximum in the back-and-forth movement. This takes place by means of rotation of the forward and rear housing parts 3, 7 relative to one another, which are therefore connected to one another by means of an articulated connection 35, 36. Because of this rotation, the angle of the inclined position between the drive axle and the axis of the back-and-forth movement of the needle 8, which changes the distance of the bearings for the drive-side end and the output side end 23, 25 of the connecting rod. The forward and rear housing parts 3, 7 are coupled with the assistance of a plastic ring 36.

A needle protrusion 37 of the needle tip with respect to the front housing opening 9 is also at its maximum. The needle protrusion 37 can be adjusted. To this end, an adjustment component 38 is supported by means of a screw connection 39. The needle protrusion 37 is adjusted by rotation (screwing) of the adjustment component 38 which thereby changes its relative position along the axis of the housing in the front housing part 3.

A closing cap 40 sits on back of the needle model 5.

FIGS. 3A to 3D show the handheld device 1 in an illustration comparable to those in FIGS. 2A to 2D in various working positions wherein the stroke or lift of the needle shaft 30 is also set at its maximum in this embodiment. In contrast with FIGS. 2A to 2D, however, the needle protrusion here is set at its minimum.

FIGS. 4A to 4D and 5A to 5D show the handheld device 1 also in various working positions, wherein the stroke of the needle shaft 30 is now minimized. In the embodiment in FIGS. 4A to 4D, the needle protrusion is maximized whereas in the embodiment in FIGS. 5A to 5D the needle protrusion is again minimized FIG. 6 shows an enlarged perspective diagram of a section of the handheld device 1 with parts of the housing 2; this shows the drive-side coupling element 20 in particular, as well as the drive-side end of the connecting rod coupling thereto and the front housing part 3, which couples to the housing 2, so that it can rotate about a limited angle, is masked out by the housing.

FIG. 7 shows an enlarged sectional diagram of the handheld device 1.

Figure 8A:
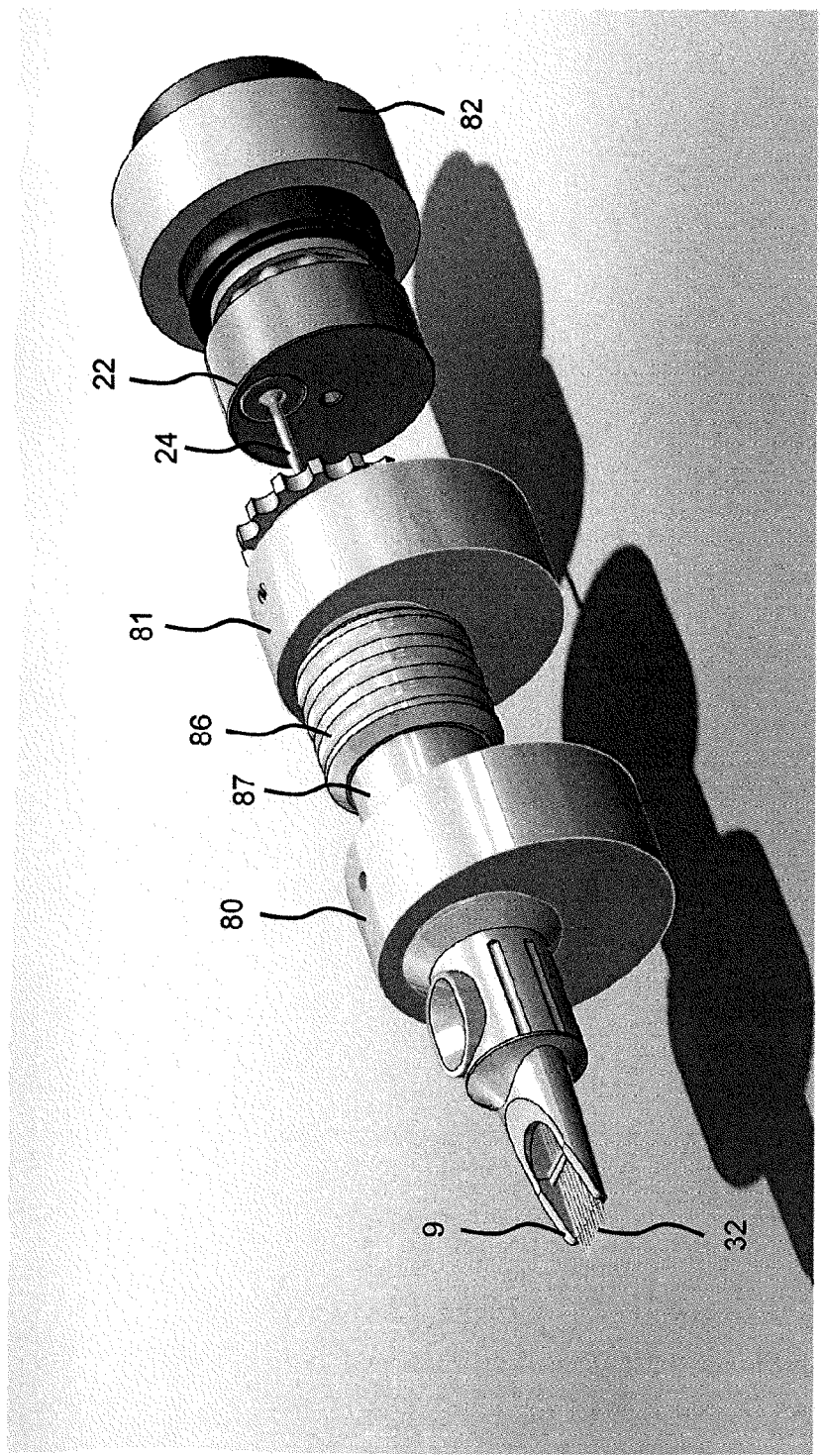

FIG. 8A shows a schematic perspective diagram of an arrangement for a handheld device for repeated puncture of skin, wherein in contrast with the embodiments in FIGS. 1 to 7, the axis of the driveshaft 21 and the shape of the linear path of movement in the back-and-forth movement of the puncture device 31 are arranged so that they are offset in parallel to one another. FIG. 8A here shows an experimental design, in which components of the handheld device are arranged on adaptors 80, 81, 82 for examination and testing purposes. Moreover, the same reference numerals are used here as in the preceding description for the same features.

Figure 8B:
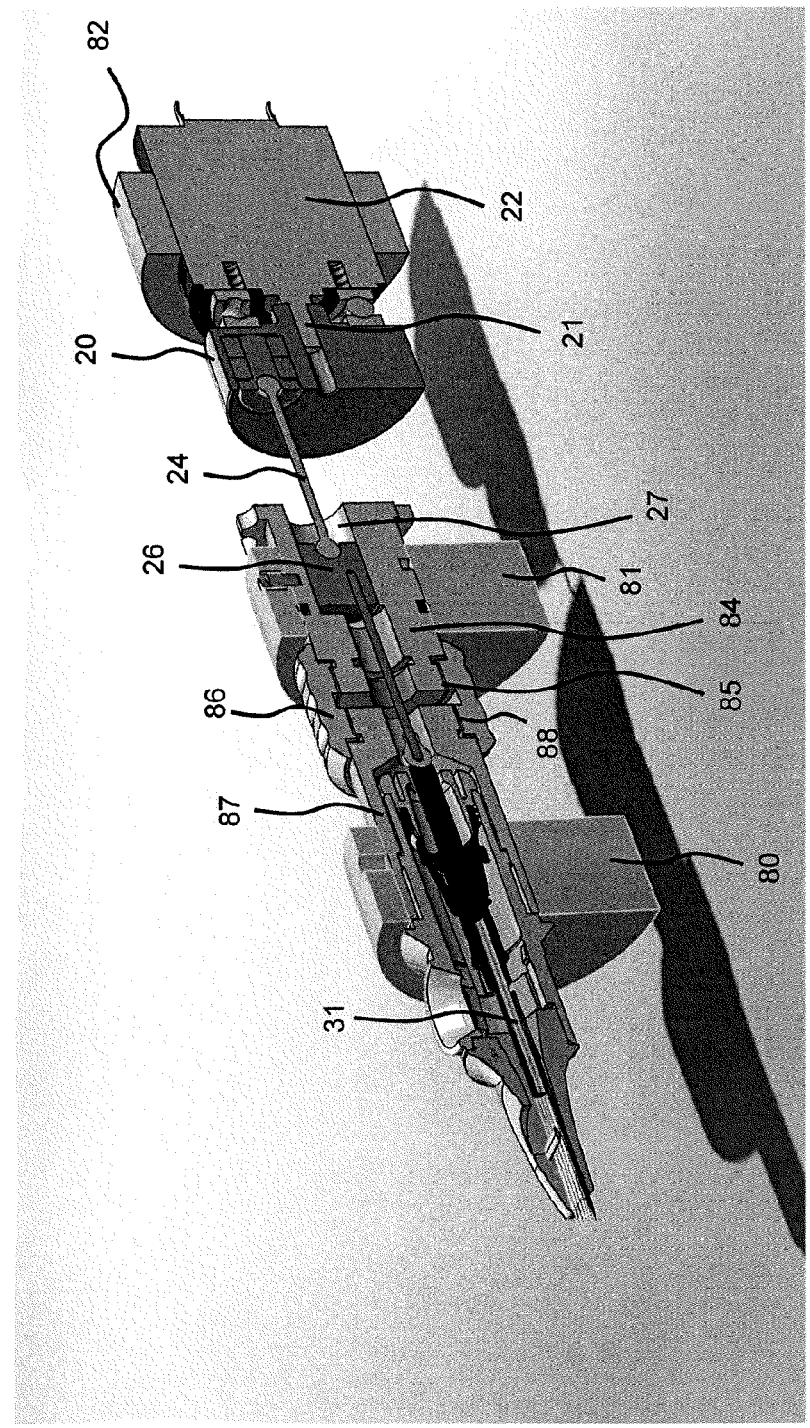
Figure 8C:
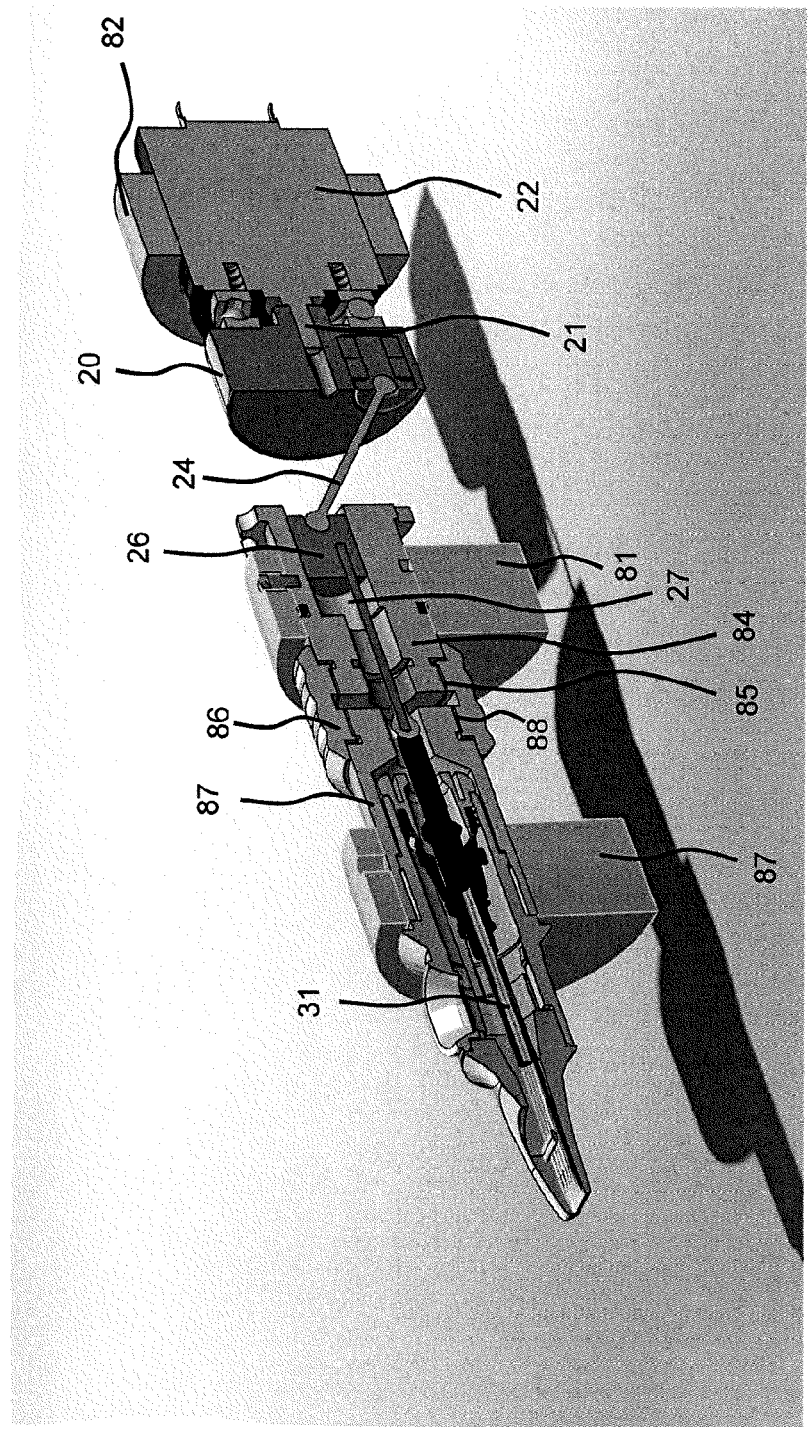
Figure 8D:
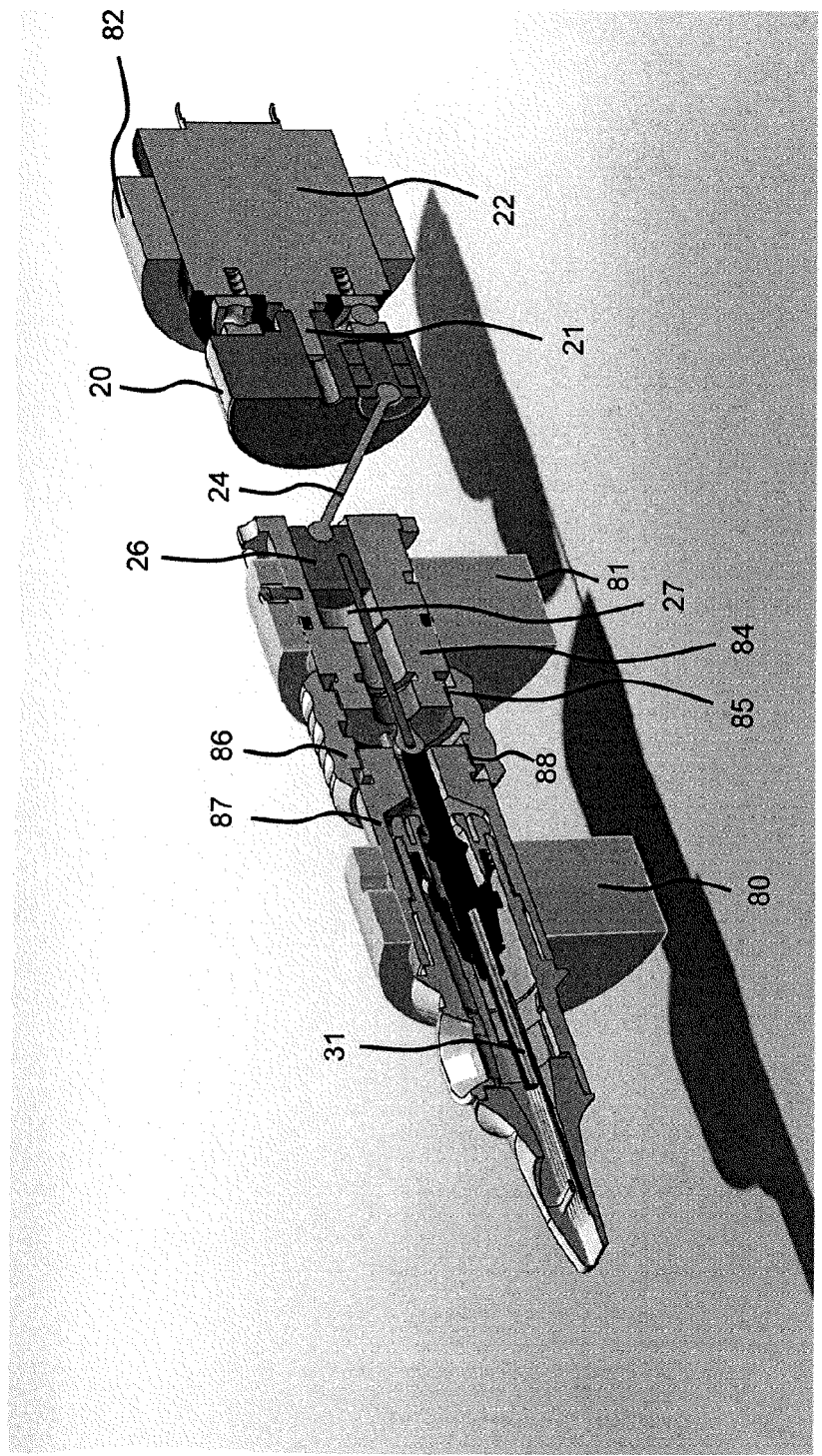

FIGS. 8B to 8D show the arrangement from FIG. 8A in different operating positions for the drive-side coupling element 20 as well as various settings for a stroke executed by the puncture device 31 and a maximum needle protrusion.

In the embodiment shown in FIGS. 8B and 8C, the stroke executed by the puncture device 31 is set at the maximum by means of a stroke setting. The distance between the drive-side and the output-side coupling elements 20, 26 is at the maximum in FIG. 8B, and it is at the minimum in FIG. 8C, wherein the conversion of the condition shown in FIG. 8D to the condition shown in FIG. 8C is achieved by a 180° rotation of the drive-side coupling element 20.

In the diagram in FIG. 8D, the stroke or lift that is carried out is set at the minimum, and the distance between the drive-side and output-side coupling elements 20, 26 is also minimal. In this embodiment variant, the stroke is set by turning a component 84, which is arranged in an eccentric position relative to the longitudinal axis of the drive, so that the component can be rotated and displaced and on which in turn the guide 27 for the output-side coupling element 26 is again formed in eccentric position to its central axis. If the component 84 is rotated about its longitudinal axis, then the central axis of the output-side coupling element 26 and thus the output side joint socket, which accommodates the output side end 25 of the connecting rod is brought into proximity of or removed away from the longitudinal axis of the drive (axial direction of the driveshaft 21) by means of additive or subtractive super-positioning of the eccentricities. The stroke is increased or decreased in this way. In terms of the design, this stroke setting results in particular in a displacement of a rear dead center of the needle movement of the puncture device 31. In doing so, the stroke setting is accomplished by varying the relative position between the movement device of the needle movement of the puncture device 31, on the one hand, in particular the direction of movement of the output-side coupling element 26 in the guide 27, and the axial direction of the driveshaft 21. A parallel offset occurs. The distance between the two parallel directions (axes) is altered to adjust the stroke.

In addition, the needle protrusion is adjustable, i.e., the extent of protrusion of the puncture needle tip 32 in the direction of the front housing opening 9. In the design in FIGS. 8B and 8C, the needle protrusion or needle retraction is at its maximum, whereas it is at its minimum in the design in FIG. 8D. The needle protrusion is set, for example, by rotation of an adjusting sleeve 86, in which a module receptacle 87 is supported by means of a screw connection 88.

To secure the needle protrusion in the stroke setting (to keep it constant), there is an axial displacement of all the components arranged at a greater distance distally in the embodiment as a function of the angle of rotation, for adjusting the stroke thanks to a control cam with the rotation of the component 84. To do so, for example, a threaded pin engages in a control cam mounted on the circumference of the adjusting sleeve 86. This control cam in turn causes a fixedly predefined axial displacement by a defined amount per change in the angle of rotation due to its angle of rotation-increase/pitch function. The stroke setting without the compensation described here can be interpreted as a combined needle-protrusion-stroke-setting, so that a separate adjustment of the needle protrusion can be omitted.

The rotational movement for adjusting the stroke can be uncoupled from the angular position of the puncture module.

In the design variant (not shown), which is based on FIG. 8, an equalizing mechanism may be provided which is suitable for compensating for the axial offset between the drive axle and the longitudinal axis of the output-side coupling element 26, such that the puncture module 5 comes to lie in the drive-side axis and the puncture movement largely takes place in this axis.

A displacement of the axis for the stroke adjustment can also take place by means of a shift or by its combination with or execution one after the other instead of by means of a rotational movement.

The conversion mechanism, which comprises in particular the drive-side coupling element 22, the rod connector 24 and the output-side coupling element 26, may be designed entirely or partially in the puncture module 5 in the various embodiments of the handheld device, wherein a detachable torque transmission of the drive device 22 to the conversion mechanism can be provided, i.e., between the drive-side coupling element 20 and the drive shaft 21 of the drive device 22 in FIG. 8B.

The puncture movement may also take place in the opposite axial direction for all variants of this drive concept, for example, when the front dead center is to be influenced by the combined stroke-needle-protrusion setting or when required by the design space, for example, when a compact short puncture device is desired instead of an elongated pin-shaped puncture device.

The features disclosed in the preceding description, the claims and the drawings may be important both individually and in any combination for the implementation of the various embodiments.

The invention claimed is:

1. A handheld device for repeated local puncture of human or animal skin, comprising:
   a housing on which a handle is formed,
   a drive device which is arranged in the housing and with which a rotating movement about an axis of rotation is supplied via a driveshaft,
   a conversion mechanism which is coupled to the driveshaft and is arranged in the housing and set up to convert the rotating movement into a driving movement along a driving movement direction, and
   a puncture device which is arranged in the housing and comprises a puncture element, which is arranged on a needle shaft that can be moved back and forth repeatedly along a path of movement together with the puncture element and is connected to the conversion mechanism,
   wherein the conversion mechanism has a rod crank device, and a stroke executed by the puncture element in moving back and forth is adjustable by altering a relative position between an axial direction of the axis of rotation and the direction of the driving movement.

2. The handheld device according to claim 1, wherein, in the rod crank device,
   a drive-side coupling element is provided, which is coupled to the driveshaft and rotates according to the rotating movement during operation,
   a proximal end of a rod connector couples to the drive-side coupling element in an articulated joint, such that the proximal end of the rod connector is moved around the axis of rotation of the driveshaft on a closed path of movement during the rotation of the drive-side coupling element, and
   a distal end of the rod connector couples to an output-side coupling element, which is coupled to the needle shaft for transferring the driving movement.

3. The handheld device according to claim 2, wherein the articulated joint between the proximal end of the rod connector and the drive-side coupling element is designed to be rotationally decoupling.

4. The handheld device according to claim 2, wherein the articulated joint between the distal end of the rod connector and the output-side coupling element is designed to be rotationally decoupling.

5. The handheld device according to claim 2, wherein the proximal end of the rod connector and the distal end of the rod connector are accommodated on the rod connector in a rotationally decoupled manner.

6. The handheld device according to claim 2, wherein the proximal end of the rod connector is connected in an articulated joint to the drive-side coupling element and/or the distal end of the rod connector is connected in an articulated joint to the output-side coupling element by means of a ball joint.

7. The handheld device according to claim 2, wherein the output-side coupling element is connected to the needle shaft via a rigid connection or is designed integrally therewith.

8. The handheld device according to claim 2, wherein the conversion mechanism has a rotational decoupling.

9. The handheld device according to claim 8, wherein the articulated joint between the proximal end of the rod connector and the drive-side coupling element is designed to be rotationally decoupling.

10. The handheld device according to claim 9, wherein the articulated joint between the distal end of the rod connector and the output-side coupling element is designed to be rotationally decoupling.

11. The handheld device according to claim 8, wherein the articulated joint between the distal end of the rod connector and the output-side coupling element is designed to be rotationally decoupling.

12. The handheld device according to claim 1, wherein the conversion mechanism has a rotational decoupling.

13. The handheld device according to claim 1, wherein a retrieval device is coupled to the needle shaft.

14. The handheld device according to claim 1, wherein the direction of the driving movement is not parallel to the axial direction of the axis of rotation.

15. The handheld device according to claim 1, wherein a maximum needle protrusion of a puncture needle tip of the puncture element is adjustable with respect to a front housing opening by means of a stroke adjustment.

16. The handheld device according to claim 1, wherein the housing is formed with a plurality of housing modules, wherein the drive device is arranged in a drive module and the puncture device is arranged in a puncture module or needle module.

* * * * *